United States Patent
Reubelt et al.

(10) Patent No.: US 10,898,336 B2
(45) Date of Patent: Jan. 26, 2021

(54) FEMORAL AND HUMERAL STEM GEOMETRY AND IMPLANTATION METHOD FOR ORTHOPEDIC JOINT RECONSTRUCTION

(71) Applicant: Tornier, Inc., Bloomington, MN (US)

(72) Inventors: Leo M. Reubelt, Hawthorne, NJ (US); Peter L. Verrillo, Wood Ridge, NJ (US)

(73) Assignee: Tornier, Inc., Bloomington, MN (US)

( * ) Notice: Subject to any disclaimer, the term of this patent is extended or adjusted under 35 U.S.C. 154(b) by 0 days.

(21) Appl. No.: 15/250,606

(22) Filed: Aug. 29, 2016

(65) Prior Publication Data

US 2016/0361173 A1    Dec. 15, 2016

Related U.S. Application Data

(63) Continuation of application No. 11/689,470, filed on Mar. 21, 2007, now abandoned.
(Continued)

(51) Int. Cl.
*A61F 2/36* (2006.01)
*A61B 17/16* (2006.01)
(Continued)

(52) U.S. Cl.
CPC .......... *A61F 2/3662* (2013.01); *A61B 17/164* (2013.01); *A61B 17/1659* (2013.01);
(Continued)

(58) Field of Classification Search
CPC .................................. A62F 2/36; A62F 2/3662
See application file for complete search history.

(56) References Cited

U.S. PATENT DOCUMENTS 3,694,820 A    10/1972    Scales et al.
3,815,157 A    6/1974    Skorecki et al.
(Continued)

FOREIGN PATENT DOCUMENTS

CH    426096    12/1966
CH    507704    5/1971
(Continued)

OTHER PUBLICATIONS

Apoil, Andre "A Condyle for the Rotator Cuff Muscles, the total shoulder prosthesis," Aesculap®, 1994.
(Continued)

*Primary Examiner* — Bruce E Snow
*Assistant Examiner* — Melissa A Hoban
(74) *Attorney, Agent, or Firm* — Knobbe Martens Olson and Bear, LLP

(57) ABSTRACT

The present inventions relate to devices and methods that improve the positioning and fit of orthopedic reconstructive joint replacement stem implants relative to existing methods. For example, an embodiment of the device provides a stem component comprising proximal and distal body portions that can be configured to mimic a geometric shape of a central cavity region created in a bone of a joint for improving conformance and fixation of the stem component thereto. Further, another embodiment provides a system of stem implants that each have a unique medial offset for facilitating the matching of an implant to the geometry of a central cavity region of a bone. Additionally, an inclination angle of a resection surface of each of the implants in the system can remain constant or vary as a function of the medial offset.

20 Claims, 16 Drawing Sheets

Related U.S. Application Data

(60) Provisional application No. 60/784,236, filed on Mar. 21, 2006.

(51) Int. Cl.
- *A61F 2/40* (2006.01)
- *A61B 90/00* (2016.01)
- *A61B 17/00* (2006.01)
- *A61F 2/30* (2006.01)

(52) U.S. Cl.
CPC ...... *A61B 17/1668* (2013.01); *A61B 17/1684* (2013.01); *A61F 2/40* (2013.01); *A61F 2/4059* (2013.01); *A61B 2017/0046* (2013.01); *A61B 2017/00464* (2013.01); *A61B 2090/062* (2016.02); *A61F 2/36* (2013.01); *A61F 2002/3054* (2013.01); *A61F 2002/30332* (2013.01); *A61F 2002/30538* (2013.01); *A61F 2002/30604* (2013.01); *A61F 2002/30607* (2013.01); *A61F 2002/30616* (2013.01); *A61F 2002/3625* (2013.01); *A61F 2002/3631* (2013.01); *A61F 2002/4018* (2013.01); *A61F 2002/4051* (2013.01); *A61F 2002/4062* (2013.01); *A61F 2002/4077* (2013.01); *A61F 2220/0033* (2013.01); *A61F 2250/0006* (2013.01); *A61F 2250/0062* (2013.01)

(56) References Cited

U.S. PATENT DOCUMENTS

| | | |
|---|---|---|
| 3,842,442 A | 10/1974 | Kolbel |
| 3,864,758 A | 2/1975 | Yakich |
| 3,869,730 A | 3/1975 | Skobel |
| 3,916,451 A | 11/1975 | Buechel et al. |
| 3,978,528 A | 9/1976 | Crep |
| 3,979,778 A | 9/1976 | Stroot |
| 3,992,726 A | 11/1976 | Freeman et al. |
| 4,003,095 A | 1/1977 | Gristina |
| 4,030,143 A | 6/1977 | Elloy et al. |
| 4,040,131 A | 8/1977 | Gristina |
| 4,054,955 A | 10/1977 | Seppo |
| 4,135,517 A | 1/1979 | Reale |
| 4,179,758 A | 12/1979 | Gristina |
| 4,206,517 A | 6/1980 | Pappas et al. |
| 4,261,062 A | 1/1981 | Amstutz et al. |
| 4,310,931 A * | 1/1982 | Muller .............. A61F 2/36 623/22.4 |
| 4,550,450 A | 11/1985 | Kinnett |
| 4,693,723 A | 9/1987 | Gabard |
| 4,795,471 A | 1/1989 | Oh |
| 4,822,370 A | 4/1989 | Schelhas |
| 4,846,840 A | 7/1989 | Leclercq et al. |
| 4,865,605 A | 9/1989 | Dines et al. |
| 4,865,609 A | 9/1989 | Roche |
| 4,892,549 A | 1/1990 | Figgie, III et al. |
| 4,919,670 A | 4/1990 | Dale et al. |
| 4,957,510 A | 9/1990 | Cremascoli |
| 4,963,155 A | 10/1990 | Lazerri et al. |
| 5,032,132 A | 7/1991 | Matsen, III et al. |
| 5,080,673 A | 1/1992 | Burkhead et al. |
| 5,080,685 A | 1/1992 | Bolesky et al. |
| 5,108,451 A * | 4/1992 | Forte .............. A61F 2/36 623/22.41 |
| 5,127,920 A | 7/1992 | MacArthur |
| 5,133,760 A | 7/1992 | Petersen et al. |
| 5,135,529 A | 8/1992 | Paxson et al. |
| 5,163,961 A | 11/1992 | Harwin |
| 5,181,928 A | 1/1993 | Bolesky et al. |
| 5,192,329 A | 3/1993 | Christie et al. |
| 5,201,882 A | 4/1993 | Paxson |
| 5,206,925 A | 4/1993 | Nakazawa et al. |
| 5,222,984 A | 6/1993 | Forte |
| 5,261,914 A | 11/1993 | Warren |
| 5,314,479 A | 5/1994 | Rockwood, Jr. et al. |
| 5,314,487 A | 5/1994 | Schryver et al. |
| 5,330,531 A | 7/1994 | Capanna |
| 5,358,526 A | 10/1994 | Tornier |
| 5,383,936 A | 1/1995 | Kubein-Meesenburg et al. |
| 5,425,779 A | 6/1995 | Schlosser |
| 5,443,519 A | 8/1995 | Averill et al. |
| 5,462,563 A | 10/1995 | Shearer et al. |
| 5,507,817 A | 4/1996 | Craig et al. |
| 5,507,818 A | 4/1996 | McLaughlin |
| 5,507,824 A | 4/1996 | Lennox |
| 5,549,682 A | 8/1996 | Roy |
| 5,580,352 A | 12/1996 | Sekel |
| 5,702,447 A | 12/1997 | Walch et al. |
| 5,702,457 A | 12/1997 | Walch et al. |
| 5,702,486 A | 12/1997 | Craig et al. |
| 5,723,018 A | 3/1998 | Cyprien et al. |
| 5,728,161 A | 3/1998 | Camino et al. |
| 5,741,335 A | 4/1998 | Gerber et al. |
| 5,755,807 A | 5/1998 | Anstaett et al. |
| 5,800,551 A | 9/1998 | Williamson et al. |
| 5,879,405 A | 3/1999 | Ries et al. |
| 5,902,340 A | 5/1999 | White et al. |
| 5,910,171 A | 6/1999 | Kummer et al. |
| 5,928,285 A | 7/1999 | Bigliani et al. |
| 5,944,758 A | 8/1999 | Mansat et al. |
| 5,961,555 A | 10/1999 | Huebner |
| 5,984,927 A | 11/1999 | Wenstrom, Jr. et al. |
| 6,015,437 A | 1/2000 | Stossel |
| 6,033,439 A | 3/2000 | Camino et al. |
| 6,045,582 A | 4/2000 | Prybyla |
| 6,045,583 A | 4/2000 | Gross et al. |
| 6,102,953 A | 8/2000 | Huebner |
| 6,129,764 A | 10/2000 | Servidio |
| 6,165,224 A | 12/2000 | Tornier |
| 6,171,341 B1 | 1/2001 | Boileau et al. |
| 6,187,012 B1 | 2/2001 | Masini |
| 6,197,062 B1 * | 3/2001 | Fenlin .............. A61F 2/4014 623/19.12 |
| 6,197,063 B1 | 3/2001 | Dews |
| 6,203,575 B1 | 3/2001 | Farey |
| 6,206,925 B1 | 3/2001 | Tornier |
| 6,228,119 B1 | 5/2001 | Ondrla et al. |
| 6,228,120 B1 | 5/2001 | Leonard et al. |
| 6,267,767 B1 | 7/2001 | Stroble et al. |
| 6,283,999 B1 | 9/2001 | Rockwood, Jr. |
| 6,312,467 B1 | 11/2001 | McGee |
| 6,334,874 B1 | 1/2002 | Tornier et al. |
| 6,364,910 B1 | 4/2002 | Schultz et al. |
| 6,368,352 B1 | 4/2002 | Camino et al. |
| 6,368,353 B1 | 4/2002 | Arcand |
| 6,398,812 B1 | 6/2002 | Masini |
| 6,406,495 B1 | 6/2002 | Schoch |
| 6,406,496 B1 | 6/2002 | Ruter |
| 6,436,144 B1 | 8/2002 | Ahrens |
| 6,436,147 B1 | 8/2002 | Zweymuller |
| 6,458,136 B1 | 10/2002 | Allard et al. |
| 6,475,243 B1 | 11/2002 | Sheldon et al. |
| 6,494,913 B1 | 12/2002 | Huebner |
| 6,506,214 B1 | 1/2003 | Gross |
| 6,508,840 B1 | 1/2003 | Rockwood, Jr. et al. |
| 6,514,287 B2 | 2/2003 | Ondrla et al. |
| 6,520,994 B2 | 2/2003 | Nogarin |
| 6,530,957 B1 | 3/2003 | Jack |
| 6,558,425 B2 | 5/2003 | Rockwood, Jr. |
| 6,569,202 B2 | 5/2003 | Whiteside |
| 6,589,281 B2 | 7/2003 | Hyde, Jr. |
| 6,589,282 B2 | 7/2003 | Pearl |
| 6,620,197 B2 | 9/2003 | Maroney et al. |
| 6,626,946 B1 | 9/2003 | Walch et al. |
| 6,648,894 B2 | 11/2003 | Abdelgany et al. |
| 6,673,114 B2 | 1/2004 | Hartdegen et al. |
| 6,673,115 B2 | 1/2004 | Resch et al. |
| 6,679,916 B1 | 1/2004 | Frankle et al. |
| 6,702,854 B1 | 3/2004 | Cheal et al. |
| 6,719,799 B1 | 4/2004 | Kropf |
| 6,723,102 B2 | 4/2004 | Johnson et al. |
| 6,736,851 B2 | 5/2004 | Maroney et al. |
| 6,746,487 B2 | 6/2004 | Scifert et al. |

(56) References Cited

U.S. PATENT DOCUMENTS

| | | |
|---|---|---|
| 6,749,637 B1 | 6/2004 | Bahler |
| 6,755,866 B2 | 6/2004 | Southworth |
| 6,761,740 B2 | 7/2004 | Tornier |
| 6,780,190 B2 | 8/2004 | Maroney |
| 6,783,549 B1 | 8/2004 | Stone et al. |
| 6,790,234 B1 | 9/2004 | Frankle |
| 6,863,690 B2 | 3/2005 | Ball et al. |
| 6,875,234 B2 | 4/2005 | Lipman et al. |
| 6,887,277 B2 | 5/2005 | Rauscher et al. |
| 6,890,358 B2 | 5/2005 | Ball et al. |
| 6,899,736 B1 | 5/2005 | Rauscher et al. |
| 6,942,699 B2 | 9/2005 | Stone et al. |
| 6,953,478 B2 | 10/2005 | Bouttens et al. |
| 6,969,406 B2 | 11/2005 | Tornier |
| 7,001,389 B1 | 2/2006 | Navarro et al. |
| 7,011,686 B2 | 3/2006 | Ball et al. |
| 7,033,396 B2 | 4/2006 | Tornier |
| 7,066,959 B2 | 6/2006 | Errico |
| 7,108,719 B2 | 9/2006 | Horber |
| 7,166,132 B2 | 1/2007 | Callaway et al. |
| 7,175,663 B1 | 2/2007 | Stone |
| 7,195,645 B2 | 3/2007 | Disilvestro et al. |
| 7,238,207 B2 | 7/2007 | Blatter et al. |
| 7,238,208 B2 | 7/2007 | Camino et al. |
| 7,309,360 B2 * | 12/2007 | Tornier .................. A61F 2/40 623/19.12 |
| 7,329,284 B2 | 2/2008 | Maroney et al. |
| 7,338,498 B2 | 3/2008 | Long et al. |
| 7,445,638 B2 | 11/2008 | Benguin et al. |
| 7,621,961 B2 | 11/2009 | Stone et al. |
| 7,749,278 B2 | 7/2010 | Frederick et al. |
| 7,758,650 B2 | 7/2010 | Dews et al. |
| 7,802,503 B2 | 9/2010 | Couvillion et al. |
| 7,819,923 B2 | 10/2010 | Stone et al. |
| 7,998,217 B1 | 8/2011 | Brown |
| 8,062,376 B2 | 11/2011 | Shultz et al. |
| 8,070,820 B2 | 12/2011 | Winslow et al. |
| 8,231,684 B2 | 7/2012 | Mutchler et al. |
| 8,236,059 B2 | 8/2012 | Stone et al. |
| 8,257,363 B2 | 9/2012 | Splieth et al. |
| 8,357,204 B2 * | 1/2013 | Ragbir .................. A61F 2/3609 623/23.15 |
| 8,512,410 B2 | 8/2013 | Metcalfe et al. |
| 8,529,629 B2 | 9/2013 | Angibaud et al. |
| 8,545,504 B2 | 10/2013 | Durand-Allen et al. |
| 8,608,805 B2 | 12/2013 | Forrer et al. |
| 8,623,092 B2 | 1/2014 | Bickley et al. |
| 8,647,387 B2 | 2/2014 | Winslow |
| 8,663,333 B2 | 3/2014 | Metcalfe et al. |
| 8,663,334 B2 | 3/2014 | Viscardi et al. |
| 8,764,845 B2 | 7/2014 | Brooks et al. |
| 8,764,846 B2 | 7/2014 | Grappiolo |
| 8,795,379 B2 | 8/2014 | Smith et al. |
| 8,845,742 B2 | 9/2014 | Kusogullari et al. |
| 8,888,855 B2 | 11/2014 | Roche et al. |
| 8,906,103 B2 | 12/2014 | Stone et al. |
| 8,945,234 B2 | 2/2015 | Humphrey |
| 9,241,803 B2 | 1/2016 | Stone et al. |
| 9,283,083 B2 | 3/2016 | Winslow et al. |
| 9,326,862 B2 | 5/2016 | Smith et al. |
| 9,421,105 B2 | 8/2016 | Metcalfe et al. |
| 9,474,618 B2 | 10/2016 | Bickley et al. |
| 9,498,344 B2 | 11/2016 | Hodorek et al. |
| 9,566,162 B2 | 2/2017 | Isch |
| 9,597,190 B2 | 3/2017 | Chavarria et al. |
| 9,603,712 B2 | 3/2017 | Bachmaier |
| 9,610,165 B2 | 4/2017 | Poncet et al. |
| 9,622,869 B2 | 4/2017 | Nerot et al. |
| 9,700,423 B2 | 7/2017 | Stone et al. |
| 9,770,334 B2 | 9/2017 | Wiley et al. |
| 9,844,439 B2 | 12/2017 | Katrana et al. |
| 9,867,710 B2 | 1/2018 | Dalla Pria et al. |
| 9,925,047 B2 | 3/2018 | Klotz et al. |
| 9,956,083 B2 | 5/2018 | Humphrey |
| 10,034,759 B2 | 7/2018 | Deransart et al. |
| 10,143,558 B2 | 12/2018 | Frankle |
| 10,143,559 B2 | 12/2018 | Ries et al. |
| 10,172,714 B2 | 1/2019 | Hatzidakis et al. |
| 10,226,349 B2 | 3/2019 | Sperling et al. |
| 10,383,734 B2 | 8/2019 | Ekelund et al. |
| 10,433,967 B2 | 10/2019 | Deransart et al. |
| 10,548,737 B2 | 2/2020 | Hodorek et al. |
| 2001/0010023 A1 | 7/2001 | Schwartz et al. |
| 2001/0011193 A1 | 8/2001 | Nogarin |
| 2001/0032021 A1 | 10/2001 | McKinnon |
| 2001/0037152 A1 | 11/2001 | Rockwood |
| 2001/0041940 A1 | 11/2001 | Pearl |
| 2001/0047210 A1 | 11/2001 | Wolf |
| 2001/0049561 A1 | 12/2001 | Dews et al. |
| 2002/0032484 A1 | 3/2002 | Hyde, Jr. |
| 2002/0049502 A1 | 4/2002 | DeCarlo et al. |
| 2002/0099381 A1 | 7/2002 | Maroney |
| 2002/0099445 A1 | 7/2002 | Maroney et al. |
| 2002/0138148 A1 | 9/2002 | Hyde, Jr. |
| 2002/0143402 A1 | 10/2002 | Steinberg |
| 2002/0151982 A1 | 10/2002 | Masini |
| 2002/0156534 A1 | 10/2002 | Grusin et al. |
| 2003/0009171 A1 | 1/2003 | Tornier |
| 2003/0028253 A1 | 2/2003 | Stone et al. |
| 2003/0097183 A1 | 5/2003 | Rauscher et al. |
| 2003/0149486 A1 | 8/2003 | Huebner |
| 2003/0171816 A1 | 9/2003 | Scifert et al. |
| 2004/0006392 A1 | 1/2004 | Grusin et al. |
| 2004/0034431 A1 | 2/2004 | Maroney et al. |
| 2004/0064105 A1 | 4/2004 | Ball et al. |
| 2004/0133276 A1 | 7/2004 | Lang et al. |
| 2004/0138754 A1 | 7/2004 | Lang et al. |
| 2004/0148033 A1 | 7/2004 | Schroeder |
| 2004/0153161 A1 | 8/2004 | Stone et al. |
| 2004/0193276 A1 | 9/2004 | Maroney et al. |
| 2004/0193277 A1 | 9/2004 | Long et al. |
| 2004/0193278 A1 | 9/2004 | Maroney et al. |
| 2004/0210317 A1 | 10/2004 | Maroney et al. |
| 2004/0220673 A1 | 11/2004 | Pria |
| 2004/0220674 A1 | 11/2004 | Pria |
| 2004/0225367 A1 | 11/2004 | Glien et al. |
| 2004/0230197 A1 | 11/2004 | Tornier et al. |
| 2004/0230311 A1 | 11/2004 | Cyprien et al. |
| 2004/0254646 A1 | 12/2004 | Stone et al. |
| 2004/0267370 A1 | 12/2004 | Ondrla |
| 2005/0008672 A1 | 1/2005 | Winterbottom et al. |
| 2005/0015154 A1 | 1/2005 | Lindsey et al. |
| 2005/0043805 A1 | 2/2005 | Chudik |
| 2005/0049709 A1 | 3/2005 | Tornier |
| 2005/0065612 A1 | 3/2005 | Winslow |
| 2005/0071014 A1 | 3/2005 | Barnett et al. |
| 2005/0085919 A1 | 4/2005 | Durand-Allen et al. |
| 2005/0085921 A1 | 4/2005 | Gupta et al. |
| 2005/0090902 A1 | 4/2005 | Masini |
| 2005/0107882 A1 | 5/2005 | Stone et al. |
| 2005/0113931 A1 | 5/2005 | Horber |
| 2005/0119531 A1 | 6/2005 | Sharratt |
| 2005/0143829 A1 | 6/2005 | Ondria et al. |
| 2005/0165490 A1 | 7/2005 | Tornier |
| 2005/0177241 A1 | 8/2005 | Angibaud et al. |
| 2005/0197708 A1 | 9/2005 | Stone et al. |
| 2005/0209700 A1 | 9/2005 | Rockwood et al. |
| 2005/0216092 A1 | 9/2005 | Marik et al. |
| 2005/0251263 A1 | 11/2005 | Forrer et al. |
| 2005/0256584 A1 | 11/2005 | Farrar |
| 2005/0267590 A1 | 12/2005 | Lee |
| 2005/0278030 A1 | 12/2005 | Tornier et al. |
| 2005/0278032 A1 | 12/2005 | Tornier et al. |
| 2005/0278033 A1 | 12/2005 | Tornier et al. |
| 2005/0288681 A1 | 12/2005 | Klotz et al. |
| 2005/0288791 A1 | 12/2005 | Tornier et al. |
| 2006/0004462 A1 | 1/2006 | Gupta |
| 2006/0009852 A1 | 1/2006 | Winslow et al. |
| 2006/0020344 A1 | 1/2006 | Shultz et al. |
| 2006/0030946 A1 | 2/2006 | Ball et al. |
| 2006/0069445 A1 | 3/2006 | Orndrla et al. |
| 2006/0241775 A1 | 10/2006 | Buss |
| 2007/0162140 A1 | 7/2007 | McDevitt |
| 2007/0173945 A1 | 7/2007 | Wiley |

(56) References Cited

U.S. PATENT DOCUMENTS

| | | |
|---|---|---|
| 2007/0179624 A1 | 8/2007 | Stone et al. |
| 2007/0225817 A1 | 9/2007 | Reubelt et al. |
| 2007/0225818 A1 | 9/2007 | Reubelt et al. |
| 2007/0225821 A1 | 9/2007 | Reubelt et al. |
| 2007/0244564 A1 | 10/2007 | Ferrand et al. |
| 2007/0244565 A1 | 10/2007 | Stchur |
| 2007/0250174 A1 | 10/2007 | Tornier et al. |
| 2008/0183297 A1 | 7/2008 | Boileau et al. |
| 2008/0228281 A1 | 9/2008 | Forrer et al. |
| 2009/0265010 A1 | 10/2009 | Angibaud et al. |
| 2009/0281630 A1 | 11/2009 | Delince et al. |
| 2010/0049327 A1 | 2/2010 | Isch et al. |
| 2010/0114326 A1 | 5/2010 | Winslow et al. |
| 2010/0268232 A1 | 10/2010 | Betz et al. |
| 2010/0288421 A1 | 11/2010 | Kujawski et al. |
| 2011/0029089 A1 | 2/2011 | Giuliani et al. |
| 2011/0060417 A1 | 3/2011 | Simmen et al. |
| 2011/0125285 A1* | 5/2011 | Ragbir .................. A61F 2/3609 623/23.15 |
| 2012/0143204 A1 | 6/2012 | Blaycock et al. |
| 2012/0253350 A1 | 10/2012 | Anthony et al. |
| 2012/0253467 A1 | 10/2012 | Frankle |
| 2013/0090736 A1 | 4/2013 | Katrana et al. |
| 2013/0197652 A1 | 8/2013 | Ekelund et al. |
| 2013/0289738 A1 | 10/2013 | Humphrey |
| 2013/0325134 A1 | 12/2013 | Viscardi et al. |
| 2014/0121709 A1 | 5/2014 | Gonzalez-Hernandez |
| 2014/0236304 A1 | 8/2014 | Hodorek et al. |
| 2014/0379089 A1 | 12/2014 | Bachmaier |
| 2015/0134066 A1 | 5/2015 | Bachmaier |
| 2015/0190237 A1 | 7/2015 | Bonin, Jr. et al. |
| 2015/0238324 A1 | 8/2015 | Nebosky et al. |
| 2015/0245912 A1 | 9/2015 | Link |
| 2015/0250601 A1 | 9/2015 | Humphrey |
| 2015/0265411 A1 | 9/2015 | Torneir et al. |
| 2016/0213480 A1 | 7/2016 | Stone et al. |
| 2016/0262902 A1 | 9/2016 | Winslow et al. |
| 2016/0324648 A1 | 11/2016 | Hodorek et al. |
| 2017/0043052 A1 | 2/2017 | San Antonio et al. |
| 2017/0049573 A1 | 2/2017 | Hodorek et al. |
| 2017/0056187 A1 | 3/2017 | Humphrey et al. |
| 2017/0030449 A1 | 11/2017 | Deransart et al. |
| 2018/0000598 A1 | 1/2018 | Amis et al. |
| 2018/0280152 A1 | 10/2018 | Mutchler et al. |
| 2018/0325687 A1 | 11/2018 | Deransart et al. |
| 2018/0333265 A1 | 11/2018 | Termanini et al. |
| 2019/0046326 A1 | 2/2019 | Ball |
| 2019/0105169 A1 | 4/2019 | Sperling |
| 2019/0231540 A1 | 8/2019 | Kim et al. |
| 2019/0231544 A1 | 8/2019 | Boileau et al. |
| 2020/0214847 A1 | 7/2020 | Hodorek et al. |

FOREIGN PATENT DOCUMENTS

| | | |
|---|---|---|
| CN | 104755047 | 7/2015 |
| DE | 19509037 | 9/1996 |
| DE | 19630298 | 1/1998 |
| DE | 102 50 390 | 5/2004 |
| DE | 10 2005 003 097 | 7/2006 |
| DE | 102008010478 | 8/2009 |
| EP | 0257359 | 3/1988 |
| EP | 0299889 | 1/1989 |
| EP | 0524857 | 1/1993 |
| EP | 0549480 | 6/1993 |
| EP | 0579868 | 1/1994 |
| EP | 0599429 | 6/1994 |
| EP | 0617934 | 10/1994 |
| EP | 0664108 | 7/1995 |
| EP | 0679375 | 11/1995 |
| EP | 0712617 | 5/1996 |
| EP | 0715836 | 6/1996 |
| EP | 0790044 A2 | 8/1997 |
| EP | 0797694 | 10/1997 |
| EP | 0807426 | 11/1997 |
| EP | 0809986 | 12/1997 |
| EP | 0864306 | 9/1998 |
| EP | 0898946 | 3/1999 |
| EP | 0898946 A1 | 3/1999 |
| EP | 0903127 | 3/1999 |
| EP | 0903128 | 3/1999 |
| EP | 0927548 | 7/1999 |
| EP | 0931522 | 7/1999 |
| EP | 1062923 | 12/2000 |
| EP | 1064890 | 1/2001 |
| EP | 1093777 | 4/2001 |
| EP | 1195149 | 4/2002 |
| EP | 1380274 | 1/2004 |
| EP | 1402854 | 3/2004 |
| EP | 1472999 A1 | 3/2004 |
| EP | 1415621 | 5/2004 |
| EP | 1 520 562 | 4/2005 |
| EP | 1520560 B1 | 10/2006 |
| EP | 1782765 | 5/2007 |
| EP | 1048274 | 9/2012 |
| EP | 2564814 | 3/2013 |
| EP | 2 604 227 | 6/2013 |
| EP | 2604225 | 6/2013 |
| FR | 2248820 | 5/1975 |
| FR | 2545352 | 11/1984 |
| FR | 2574283 | 6/1986 |
| FR | 2652498 | 4/1991 |
| FR | 2664809 | 1/1992 |
| FR | 2699400 | 6/1994 |
| FR | 2721200 | 12/1995 |
| FR | 2726994 | 5/1996 |
| FR | 2737107 | 1/1997 |
| FR | 2 758 256 | 7/1998 |
| FR | 2773469 | 7/1999 |
| FR | 2835425 | 8/2003 |
| FR | 2836039 | 8/2003 |
| FR | 2 932 678 | 12/2011 |
| FR | 2997290 | 11/2015 |
| FR | 3 025 089 | 3/2016 |
| GB | 1 504 055 | 3/1978 |
| JP | 2004-121850 | 4/2004 |
| JP | 2006-095300 | 4/2006 |
| SU | 749392 | 7/1980 |
| WO | WO 91/07932 | 6/1991 |
| WO | WO 93/09733 | 5/1993 |
| WO | WO 96/17553 | 6/1996 |
| WO | WO 98/46172 | 10/1998 |
| WO | WO 99/49792 | 10/1999 |
| WO | WO 99/65413 | 12/1999 |
| WO | WO 00/15154 | 3/2000 |
| WO | WO 00/41653 | 7/2000 |
| WO | WO 00/74554 | 12/2000 |
| WO | WO 01/47442 | 7/2001 |
| WO | WO 02/39931 | 5/2002 |
| WO | WO 02/39933 | 5/2002 |
| WO | WO 02/067821 | 9/2002 |
| WO | WO 03/005933 | 1/2003 |
| WO | WO 03/094806 | 11/2003 |
| WO | WO 2004/080331 | 9/2004 |
| WO | WO 2006/126238 | 11/2006 |
| WO | WO 07/109319 | 2/2007 |
| WO | WO 2007/084939 | 7/2007 |
| WO | WO 07/109291 | 9/2007 |
| WO | WO 07/109340 | 9/2007 |
| WO | WO 2007/082925 | 10/2007 |
| WO | WO 2008/000928 | 1/2008 |
| WO | WO 2008/050091 | 5/2008 |
| WO | WO 2008/109751 | 9/2008 |
| WO | WO 2013/064569 | 5/2013 |
| WO | WO 2014/005644 | 1/2014 |
| WO | WO 2014/067961 | 5/2014 |
| WO | WO 2014/178706 | 11/2014 |
| WO | WO 2015/112307 | 7/2015 |
| WO | WO 2016/094739 | 6/2016 |
| WO | WO 2017/184792 | 10/2017 |
| WO | WO 2019/053576 | 3/2019 |
| WO | WO 2019/106276 | 6/2019 |

(56) References Cited

FOREIGN PATENT DOCUMENTS

| WO | WO 2019/106277 | 6/2019 |
|---|---|---|
| WO | WO 2019/178104 | 9/2019 |

OTHER PUBLICATIONS

Beuchel M.D., Frederick F. "Beuchel-Pappas™ Modular Salvage Shoulder System," Endotec, Inc., 2000.
Beuchel M.D., Frederick F. "Beuchel-Pappas™ Resurfacing Shoulder System," Endotec, Inc., 2000.
Beuchel M.D., Frederick F. "Beuchel-Pappas™ Total Shoulder System," Endotec, Inc., 2000.
Boileau et al., U.S. Appl. No. 12/020,913, entitled "Method and Apparatus for Fitting a Shoulder Prosthesis" filed Jan. 28, 2008.
Boileau et al., "Adaptability and modularity of shoulder prosthese," *Maitrise Orthopedique*, http://www.maitrise-orthop.com/corpusmaitri/orthopaedic/prothese_epaule_orthop/boileau_us.shtml, Jan. 3, 2006.
Boileau et al., "Arthroscopic Repair of Full-Thickness Tears of the Supraspinatus: Does the tendon really heal?," *The Journal of Bone and Joint Surgery, Inc.*, pp. 1229-1240, 2005.
Cofield, M.D., Robert H., "Cofield$^2$ Total Shoulder System, Surgical Technique," Smith & Nephew, 1997.
Fenlin Jr., M.D. John M., Symposium on Surgery of the Shoulder, "Total Glenohumeral Joint Replacement," *Orthopedic Clinics of North America*, vol. 6, No. 2, Apr. 1975, pp. 565-583.
Hertel M.D., PD, Ralph. "Technical considerations for implantation of EPOCA glenoid components (Leseprobe)," *Epoca Newsletter*, May 14, 2001.
Mansat, Michel, "Neer 3™, Surgical Technique for Fractures," Smith & Nephew, 2000.
"Anatomic Glenoid, Surgical Technique," Smith & Nephew, 2000.
"Anatomical Shoulder™—Cemented Shoulder Prosthesis Product Information and Surgical Technique," Sulzer Medica, 2000.
"Anatomical Shoulder™ System Surgical Technique—Removeable head option for improved surgical results," Zimmer, Inc., 2004.
"Anatomical Shoulder™ System—The new removable head option," Zimmer Inc., 2004.
"Bigliani/Flatow®—The Complete Shoulder Solution, Designed by Shoulder Surgeons for Shoulder Surgery," Zimmer, Inc., 2001.
"Bigliani/ Flatow®—The Complete Shoulder Solution, 4-Part Fracture of the Humerus Surgical Technique," Zimmer, Inc., 2000.
"Bio-Modulare® / Bi-Polar Shoulder Arthroplasty," Biomet, Inc., 1997.
"Bio-Modular® Choice, Shoulder System," Biomet Orthopedics, Inc., 2004.
"Bio-Modular Total Shoulder Surgical Technique," Biomet Orthopedics, Inc., 2001.
"Copeland™ Humeral Resurfacing Head," Biomet Orthopedics, Inc., 2001.
"Delta CTA™ Reverse Shoulder Prosthesis," DePuy International, Ltd., 2004.
"Global C.A.P.™ Surgical technique, resurfacing humeral head implant," DePuy International, Ltd., 2004.
"Offset Head, Bio-Modular® Total Shoulder," Biomet, Inc., 2000.
PCT International Search Report and Written Opinion from related PCT application No. PCT/07/07059 dated Mar. 12, 2008.
Supplementary European Search Report and European Search Opinion dated Nov. 30, 2009 for EP07753667.
"Tornier Surgical Technique Addendum, Tornier Aequalis® Reversed Hemi-Adaptor Technique," Tornier, Inc., Aug. 8, 2005.
"Tornier Surgical Technique Addendum, Aequalis® Reversed Shoulder Polyethylene Insert," Tornier, Inc., Aug. 8, 2005.
"Tornier Aequalis® Reversed 2 Prong Capsular Retractor," Tornier, Inc., Oct. 8, 2005.
"Tornier Aequalis® Reversed Shoulder G2 Baseplate," Tornier, Inc., Oct. 8, 2005.
"Zimmer® Bigliani/ Flatow®—The Complete Shoulder Solution, Total Shoulder Arthroplasty Surgical Technique," Zimmer, Inc., 2003.
"Zimmer® Shoulder Retractors," Zimmer, Inc., 2000.
International Search Report and Written Opinion for PCT/EP2012/0171618 dated Apr. 12, 2013 in 20 pages.
European Search Report for EP Application No. 11306724.3 dated May 25, 2012 in 6 pages.
International Search Report and Written Opinion for PCT/EP2013/072634 dated Apr. 7, 2014 in 18 pages.
Mole, M.D. et al., "Aequalis—Reversed™ Shoulder Prosthesis, Surgical Technique," Tornier, Inc., 2004.
"Aequalis—Fracture Shoulder Prosthesis—Surgical Technique," Tornier, Inc., 2002.
"Aequalis®—Glenoid Keeled and Pegged—Surgical Technique," Tornier, Inc., 2003.
"Aequalis® Press-Fit Shoulder Prosthesis—Surgical Technique," Tornier, Inc., 2002.
"Surgical Technique, Total Elbow Prosthesis," Latitude®, Tornier Surgical Implants., 2007.
Barth, et al., "Is global humeral head offset related to intramedullary canal width? A computer tomography morphometric study," Journal of Experimental Orthopaedics, 2018, vol. 5, pp. 1-8.
Biomet Orthopedics, "Comprehensive® Shoulder System, Surgical Technique", 2007.
Boileau, et al., "The Three-Dimensional Geometry of the Proximal Humerus: Implications for Surgical Technique and Prosthetic Design," J Bone Joint Surg, Sep. 1997, vol. 79-B, Issue 5, pp. 857-865.
Delta, Delta CTA Reverse Shoulder Prosthesis, Surgical Technique, DePuy a Johnson & Johnson company, 2004.
Depuy, "Global™ Fx Shoulder Fracture System, Surgical Technique", 1999.
Depuy Synthes, "Global® UNITE Platform Shoulder System, Product Rationale & Surgical Technique", 2013.
DJO Surgical, "DJO Surgical Shoulder Solutions—Reaching Higher by Design", 2013.
Exactech, "Equinoxe Platform Shoulder System", 2014.
FH Orthopedics, "Arrow, Prothese d'epaule Universelle (Universal shoulder prosthesis)", Nov. 2009.
Integra, Titan™ Reverse Shoulder System, Surgical Technique, 2013.
JRI Orthopaedics, "VAIOS® Shoulder System", 2011.
Levy et al., "Reverse Shoulder Prosthesis for Acute Four-Part Fracture: Tuberosity Fixation Using a Horseshoe Graft", J Orthop Trauma, vol. 25, No. 5, May 2011.
Routman, et al., "Reverse Shoulder Arthroplasty Prosthesis Design Classification System," Bulletin of the Hospital for Joint Diseases, 2015, vol. 73 (Suppl 1), pp. S5-S14.
Stryker Orthopaedics, "ReUnion Fracture System Surgical Protocol", 2007.
Tornier, "Aequalis Ascend Flex Convertible Shoulder System", Feb. 8, 2016.
Zimmer, "Anatomical Shoulder™ Fracture System, Surgical Technique", 2010.
Zimmer®, "Trabecular Metal™ Humeral Stem—Enabling fracture healing", 2009.
Search Report and Written Opinion issued in French Application No. 14 62206, dated Jul. 31, 2015, in 7 pages.
International Search Report and Written Opinion for PCT/US15/65126 dated Apr. 28, 2016 in 18 pages.

\* cited by examiner

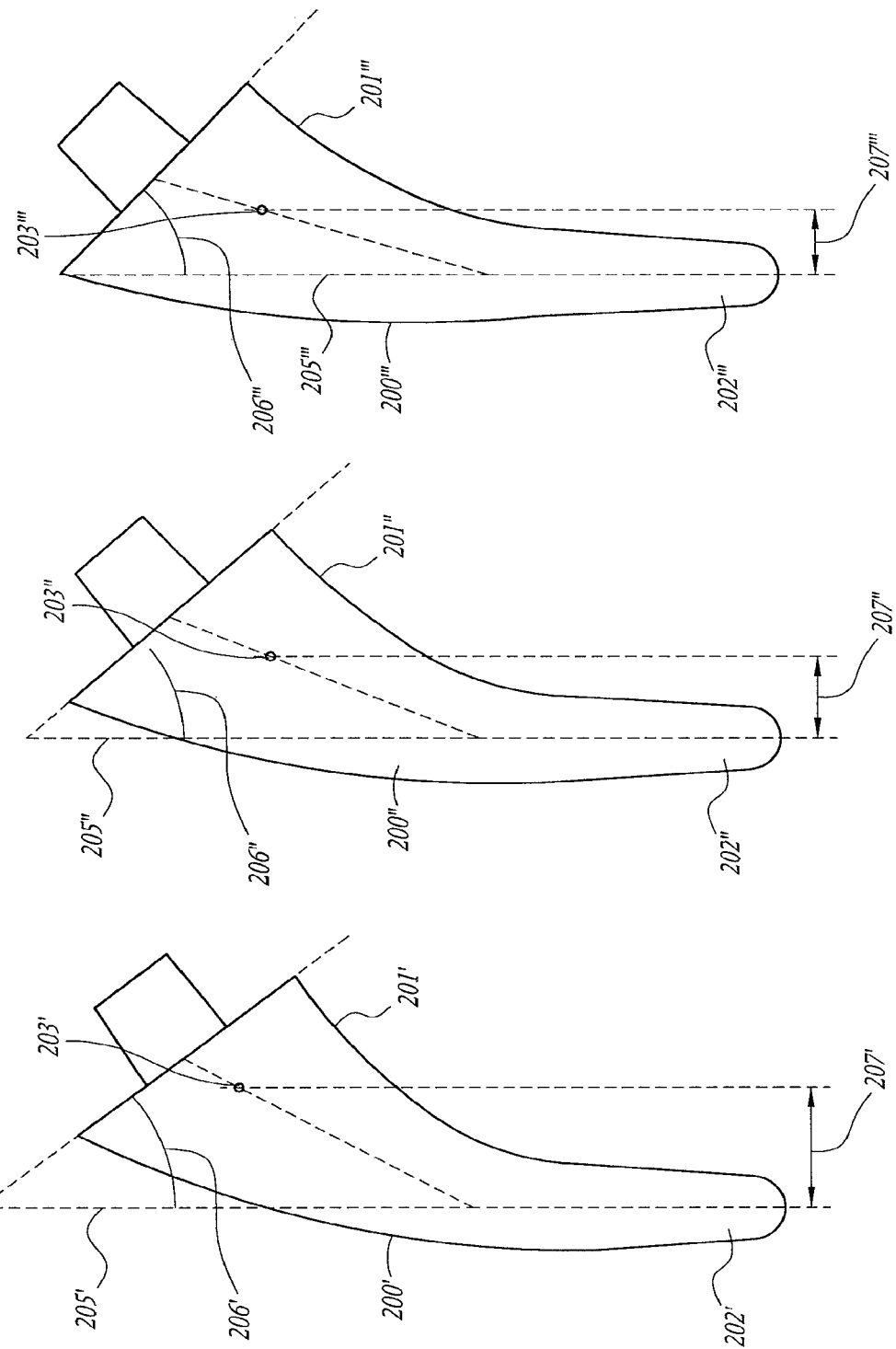

FEMORAL AND HUMERAL STEM GEOMETRY AND IMPLANTATION METHOD FOR ORTHOPEDIC JOINT RECONSTRUCTION

PRIORITY INFORMATION

The present application is a continuation of U.S. application Ser. No. 11/689,470, filed Mar. 21, 2007 titled "FEMORAL AND HUMERAL STEM GEOMETRY AND IMPLANTATION METHOD FOR ORTHOPEDIC JOINT RECONSTRUCTION," which claims the priority benefit under 35 U.S.C. § 119(e) to U.S. Provisional Patent Application 60/784,236, filed Mar. 21, 2006, the entire contents of which are expressly incorporated by reference herein.

BACKGROUND

Field of the Inventions

The present inventions relates generally to orthopedic implants, and more specifically, to a reconstructive joint replacement implant and a method of positioning and fitting such an implant.

Description of the Related Art

Anatomically, a joint is generally a movable junction between two or more bones. As used herein, the term "joint" is a broad term that is meant to include the different kinds of ligaments, tendons, cartilages, bursae, synovial membranes and bones comprising the mobile skeletal system of a subject in various quantities and configurations.

For example, the hip joint is a ball and socket joint comprising the "ball" at the head of the thigh bone (femur) with a cup-shaped "socket" (acetabulum) in the pelvic bone. The ball normally is held in the socket by powerful ligaments that form a complete sleeve around the joint (i.e., the joint capsule). The joint capsule has a delicate lining (the synovium). Cartilage, which covers the head of the femur and lines the socket, cushions the joint, and allows the bones to move on each other with very little friction. In a normal hip joint, the spherical head of the thighbone (femur) moves inside the acetabulum of the pelvis. Normally, all of these components replace the worn-out hip socket.

The shoulder is the body's most mobile joint, in that it can turn in many directions. The shoulder is a ball-and-socket joint that is made up of three bones: the upper arm bone (humerus), shoulder blade (scapula) and collarbone (clavicle). In the shoulder, two joints facilitate shoulder movement. The acromioiclavicular (AC) joint joins one end of the collarbone with the shoulder blade; it is located between the acromion (the part of the scapula that forms the highest point of the shoulder) and the clavicle. The other end of the collarbone is joined with the breastbone (sternum) by the sternoclavicular joint. The glenohumeral joint, commonly called the shoulder joint, is a ball-and-socket type joint that helps move the shoulder forward and backward and allows the arm to rotate in a circular fashion or hinge out and up away from the body. The ball of glenohurneral joint is the top, rounded portion of the humerus; the socket, or glenoid, is a dish-shaped part of the outer edge of the scapula into which the ball fits. The socket of the glenoid is surrounded by a soft-tissue ring of fibrocartilage (the glenoid labrum) that runs around the cavity of the scapula (glenoid cavity) in which the head of the humerus fits. The labrum deepens the glenoid cavity and effectively increases the surface of the shoulder joint, which helps stabilize the joint.

The bones of the shoulder are held in place by muscles, tendons (tough cords of tissue that attach the shoulder muscles to bone and assist the muscles in moving the shoulder) and ligaments (bands of fibrous tissue that connects bone to bone or cartilage to bone, supporting or strengthening a joint). A smooth, durable surface (the articular cartilage) on the head of the arm bone, and a thin lining (synovium) allows smooth motion of the shoulder joint. The joint capsule, a thin sheet of fibers that encircles the shoulder joint, allows a wide range of motion yet provides stability of the joint. The capsule is lined by a thin, smooth synovial membrane. The front of the joint capsule is anchored by three geneohumeral ligaments.

The rotator cuff, a structure composed of tendons and associated muscles that holds the ball at the top of the humerus in the glenoid socket, covers the shoulder joint and joint capsule. The rotator cuff provides mobility and strength to the shoulder joint. A sac-like membrane (bursa) between the rotator cuff and the shoulder blade cushions and helps lubricate the motion between these two structures.

The shoulder is an unstable joint easily subject to injury because of its range of motion, and because the ball of the humerus is larger than the glenoid that holds it. To remain stable, the shoulder must be anchored by its muscles, tendons and ligaments. Some shoulder problems arise from the disruption of these soft tissues due to injury or overuse, or underuse of the shoulder. Other problems can arise from degenerative processes.

For example, instability of the shoulder joint can refer to situations that occur when one of the shoulder joints moves or is forced out of its normal position. The two basic forms of shoulder instability are subluxations and dislocations. A partial or incomplete dislocation of the shoulder joint (subluxation) means the head of the humerus is partially out of the socket (glenoid). A complete dislocation of the shoulder joint means that the head of the humerus is completely out of the socket. Anterior instability, for example, can refer to a type of shoulder dislocation where the shoulder slips forward, meaning that the humerus moved forward and down out of its joint. Anterior instability may occur when the arm is placed in a throwing position. Both partial and complete dislocation cause pain and unsteadiness in the shoulder joint. Patients with repeat dislocation usually require surgery.

Bursitis or tendonitis can occur with overuse from repetitive activities, which cause rubbing or squeezing (impingement) of the rotator cuff under the acromion and in the acromioclavicular joint. Partial thickness rotator cuff tears, most often the result of heavy lifting or falls, can be associated with chronic inflammation and the development of spurs on the underside of the acromion or the AC joint. Full thickness rotator cuff tears most often are the result of impingement.

Osteoarthritis and rheumatoid arthritis can cause destruction of the shoulder joint and surrounding tissue and degeneration and tearing of the capsule or rotator cuff. In osteoarthritis, the articular surface of the joint wears thin. Rheumatoid arthritis is associated with chronic inflammation of the synovium lining, which can produce substances that eventually destroy the inner lining of the joint, including the articular surface.

Shoulder replacement is recommended for subjects with painful shoulders and limited motion. The treatment options are either replacement of the head of the humerus or replacement of the entire socket. However, currently available treatment options are less than adequate in restoring shoulder joint function. For example, just as muscles get stronger through use, the density and strength of bone varies with respect to the bone's load history. To ensure proper bone loading and good bone health, accurate implant placement, good bone fit, and restoration of a healthy anatomic position is critical. Existing devices have focused on modifying only the most proximal portion of the stem geometry, known as the neck, to adjust for different angles but do not accommodate variation of the proximal body shape.

SUMMARY

Currently, most humeral stems are implanted using a fairly common procedure. First the head is resected and the humeral canal is reamed to a best fit diameter. The humerus is then broached or reamed, using the canal as a guide, to accept the proximal body. One aspect of the present inventions is that this method poses several basic problems. First, because the distal stem is meant to be a tight fit with respect to the reamed cavity, it dictates the position of the stem and therefore, the position of the head. Since the size, location, and orientation of the head with respect to the humeral canal vary greatly from person to person, a single stem geometry per size cannot accommodate natural head placement or proximal body shape. Consequently, head placement is typically adjusted by rotating the prosthetic head around an eccentric taper. This typically results in a proximal fit that is poor because rotating an eccentric head adjusts both posterior and medial head location at the same time, virtually excluding the possibility of perfect placement. Similarly, since proximal body position and orientation are governed by the distal canal, the proximal body must be made small enough to fit the smallest possible envelope within the proximal humerus. This excessively small proximal body causes poor proximal fixation and leads to over-reliance on distal fixation. Over time, when too much emphasis is placed on distal fixation, the strength of the proximal bone begins to deteriorate. This, in turn leads to stem loosening and potentially fracture. While some companies have tried to improve upon this model by offering different neck angles, they typically use the same proximal body geometry and simply vary the resection angle. While this may improve head center placement, it offers little to accommodate varying shapes of the proximal body.

Accordingly, an embodiment of the present inventions is an orthopedic device for joint reconstruction that comprises an implantable stem component comprising a proximal section or proximal body portion. The proximal body of the stem component can be inserted into a central cavity region created in a bone of a joint. According to one aspect, the orthopedic device optionally comprises a distal section or distal body portion, wherein the distal section of the implantable stem component is placed at least one distal stem angle with respect to the proximal body component of the implantable stem component of the device. In this regard, a longitudinal axis of the distal body portion can be oriented at a discrete angle with respect to a neck axis of the proximal body portion.

In accordance with another embodiment, the stem component can taper from the proximal body portion toward the distal body portion to define medial and lateral curved surfaces. The medial and lateral curved surfaces can be configured to mimic the geometric shape of the bone for improving conformance and fixation of the stem component to the central cavity region of the bone. In this regard, the proximal body of the stem component can be inserted into a central cavity region created in the bone of a joint. The attachment portion can be tapered. Further, the bone can be a humerus. The humerus can comprise a proximal portion having a shape and a distal portion. The medial and lateral curved surfaces can conforms to the shape of the proximal portion of the implant. Further, the distal section of the stem component can have a cylindrical, elliptical, tapered, or irregular shape. Additionally, the distal body portion of the stem component can further comprise at least one feature selected from the group consisting of: a groove, a slot, a cutout, and a protrusion.

According to another aspect, the joint is a hip joint. According to another aspect, the joint is a shoulder joint. According to another aspect, the bone is a humerus. According to another aspect, the humerus comprises a proximal portion having a shape and a distal portion. According to another embodiment, the proximal body shape of the device conforms to the shape of the proximal portion of the humerus. According to another aspect, the bone is a femur. According to another aspect, the distal section of the stem component of the device has a tapered shape. According to another aspect, the distal section of the stem component of the device has a cylindrical, elliptical, tapered, or irregular shape. According to another aspect, the distal section of the stem component of the device further comprises at least one feature selected from the group consisting of a groove, a slot, a cutout, and a protrusion. According to another aspect, the distal section of the stem component of the device further comprises a ball.

In another embodiment, a system of orthopedic devices for joint reconstruction surgery is provided. The system can comprise a plurality of stem components, wherein each stem component comprising a distal body portion and a proximal body portion. The stem component can be sized and configured to be implanted to within a cavity of a bone. The distal body portion can define a longitudinal axis, and the proximal body portion can define a neck axis and a head center. Further, the proximal body portion can comprise a resection surface. The head center can be spaced from the longitudinal axis at a medial offset, and the resection surface can be oriented at an inclination angle with respect to the longitudinal axis. In such an embodiment, each stem component of the system can be configured with a different medial offset when compared to other of the stem components of the system. The system can thus provide a variety of potential matching geometries for a surgeon when performing the joint reconstruction surgery. The proximal body of a given stem component can be insertable into a central cavity region created in a bone of the joint.

In an embodiment of the system, each stem component of the system can have the same inclination angle. Further, the inclination angle of each stem component can vary as a function of the medial offset of the respective stem component. In some embodiments, the system can be configured such that each of the stem components of the system has a medial offset of between approximately 4 mm and approximately 15 mm. In addition, in other embodiments, the medial offset can be varied while the inclination angle is constant.

The system can include, for example, at least three stem components. Accordingly, a first stem component can have a medial offset of approximately 12 mm, a second stem component can have a medial offset of approximately 8 mm, and a third stem component can have a medial offset of approximately 5 mm. Additionally, the first stem component can have an inclination angle of approximately 44 degrees, the second stem component can have an inclination angle of approximately 49 degrees, and the third stem component can have an inclination angle of approximately 54 degrees. The inclination angle can be between approximately 30 degrees and approximately 55 degrees.

Further, in a method of implanting an orthopedic reconstructive joint replacement stem implant is also provided in accordance with another embodiment. The method can comprise: resecting a head of a bone of a joint; using a single instrument to successively broach and ream a central cavity region in the bone of the joint; and inserting a proximal body portion of the stem implant into the central cavity region of the bone of the joint. In particular, embodiments disclosed herein can facilitate the insertion of the proximal body portion into the central cavity region of the bone of the joint can be performed without damaging the supraspinatus. The method can further comprise the step of resecting a neck of the bone of the joint. In this method, the bone can be, for example, a femur or a humerus. Also, the joint can be, for example, a hip joint or a shoulder joint.

Another embodiment of the method can further comprise the step of selecting a stem implant in response to a geometric shape of the central cavity region of the bone. As mentioned above with respect to an embodiment of the stem implant, the stem implant can taper from the proximal body portion toward a distal body portion to define medial and lateral curved surfaces. Thus, the method can be implemented such that the medial and lateral curved surfaces can be configured to mimic the geometric shape of the central cavity region of the bone for improving conformance and fixation of the stem implant to the central cavity region of the bone.

In yet another embodiment, an instrument is provided for creating a central cavity region in a bone of a joint. The instrument comprises a broaching section, a reaming section, and a handle. The reaming section can be disposed at a distal end of the instrument. The reaming section can be sized and configured to facilitate reaming of the bone. The broaching section can be disposed axially adjacent to the reaming section and can be sized and configured to facilitate broaching of the central cavity region of the bone successive to the reaming of the bone by the reaming section. The handle can be disposed at a proximal end of the instrument and being coupled to the broaching and reaming sections for facilitating driving of the broaching and reaming sections.

BRIEF DESCRIPTION OF THE DRAWINGS

FIG. 11A is a side view of an implant of a system of implants wherein an inclination angle of the implant changes relative to a medial offset thereof, according to an embodiment.

FIG. 11B is a side view of another implant of the system, according to another embodiment.

FIG. 11C is a side view of yet another implant of the system, according to yet another embodiment.

DETAILED DESCRIPTION OF THE PREFERRED EMBODIMENTS

Figure 1:
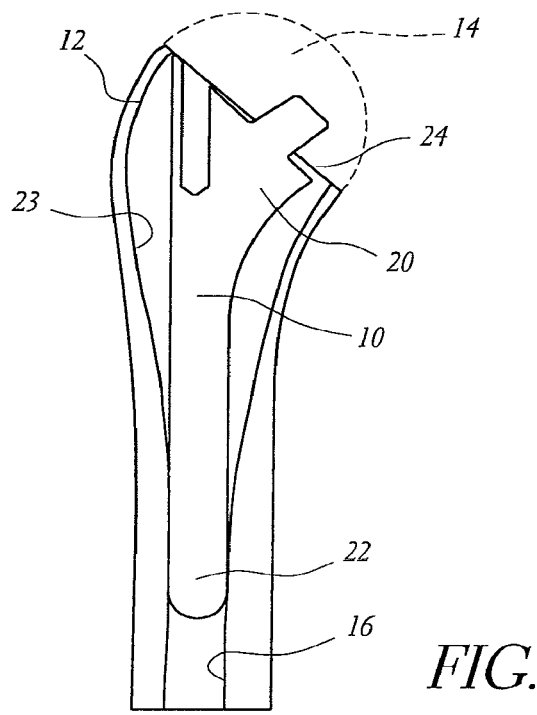
FIG. 1 is a side cross-sectional view of a prior art implant with a distal stem inserted into a humeral canal.

As used herein, the term "stem" is a broad term that is used to designate a device that is implanted into the bone for the purpose of supporting a functional component of a joint replacement and resisting the loads applied to the functional component. For example, a stem can be a device implanted into a humerus or femur to support a modular prosthetic humeral or femoral head (i.e. the supported structure). In other embodiments, the supported structure can be an integral part of the stem, as with a monolithic stem and head. Femoral and humeral stems typically include distal and proximal sections as well as a taper or other coupling device to which the functional component is attached. Additionally, femoral stems typically include a neck section that extends the distance between the proximal section and the head. The neck is not embedded in the bone, but sits proud. As used herein, the term "neck" can refer to the portion of a femoral stem that does not reside within the femur bone, and extends the distance between the proximal body and the head.

As used herein, the term "proximal body" can refer to the portion of the humeral or femoral stem that resides within the bone and is nearer to the head (more proximal). The proximal limit of the proximal body is typically denoted by the resection plane or coupling device. The distal limit of the proximal body is typically denoted by a transition from a substantially diverging shape to a slightly diverging or substantially elongated shape. These shapes are intended to somewhat mimic the shapes of the bone in their corresponding locations.

As used herein, the term "distal region" can refer to the portion of the humeral or femoral stem that resides in the bone and is farther from the head. The proximal limit of the distal region is typically denoted by a transition from a slightly diverging or substantially elongated shape, to a substantially diverging shape. These shapes are intended to somewhat mimic the shapes of the bone in their corresponding locations.

As used herein, the term "distal stem angle" can refer to the angle between the best fit central axis of the distal region of the stem and the resection plane.

As used herein, the term "cavity" can refer to the entire prepared hole in which the stem will be implanted. When the cavity is referred to as "central," a proximal location is implied because the distal humerus and femur are very elongated distally and consequently dictate central placement.

As used herein, the term "bone canal" can refer to the portion of the humerus or femur that is substantially elongated and accepts the distal region of the stem. The proximal limit of the distal region is typically denoted by a transition from a slightly diverging or substantially elongated shape, to a substantially diverging shape.

As used herein, the term "broach" can refer to a bone-cutting tool comprising a series of progressively taller points mounted on a single piece of metal, typically used to enlarge a circular hole into a larger noncircular shape such as a square or other desired shape. The amount of material removed by each broach tooth (or chisel) varies with the material being cut. A broach also may also be designed to be pushed or pulled through an existing hole. The term "broaching" as used herein, can refer to this bone-removal process.

As used herein, the term "reaming" can refer to a process whereby a hole is enlarged to an accurate size. Although generally reaming must be preceded by a drilling or boring operation, that is not true in embodiments disclosed herein, for example, where the starting material is a hole or other shape that is being cleaned up. Reaming can also be performed on surfaces such as a sphere or other concave or convex surfaces as it is when a glenoid is reamed with a spherical reamer. The term "resect," "resecting," or "resection" as used herein can refer to a process whereby a portion of a structure is cut off or cut out.

The term "subject" as used herein includes animals of mammalian origin, including humans. When referring to animals that typically have one end with a head and mouth, with the opposite end often having the anus and tail, the head end is referred to as the cranial end, while the tail end is referred to as the caudal end. Within the head itself, rostral can refer to the direction toward the end of the nose, and caudal is used to refer to the tail direction. The surface or side of an animal's body that is normally oriented upwards, away from the pull of gravity, is the dorsal side; the opposite side, typically the one closest to the ground when walking on all legs, swimming or flying, is the ventral side. On the limbs or other appendages, a point closer to the joint contact is "proximal"; a point farther away is "distal." This principle shall be followed in relation to embodiments of the apparatuses disclosed herein; a point closer to the main body of the apparatus shall be referred to as "proximal;" a point farther away shall be referred to as "distal."

Three basic reference planes are used in zoological anatomy. A "sagittal" plane divides the body into left and right portions. The "midsagittal" plane is in the midline, i.e. it would pass through midline structures such as the spine, and all other sagittal planes are parallel to it. A "coronal" plane divides the body into dorsal and ventral portions. A "transverse" plane divides the body into cranial and caudal portions.

When referring to humans, the body and its parts are always described using the assumption that the body is standing upright. Portions of the body which are closer to the head end are "superior" (corresponding to cranial in animals), while those farther away are "inferior" (corresponding to caudal in animals). Objects near the front of the body are referred to as "anterior" (corresponding to ventral in animals); those near the rear of the body are referred to as "posterior" (corresponding to dorsal in animals). A transverse, axial, or horizontal plane is an X-Y plane, parallel to the ground, which separates the superior/head from the inferior/feet. A corona] or frontal plane is an Y-Z plane, perpendicular to the ground, which separates the anterior from the posterior. A sagittal plane is an X-Z plane, perpendicular to the ground and to the corona] plane, which separates left from right. The midsagittal plane is the specific sagittal plane that is exactly in the middle of the body.

Structures near the midline are called medial and those near the sides of animals are called lateral. Therefore, medial structures are closer to the midsagittal plane, lateral structures are further from the midsagittal plane. Structures in the midline of the body are median. For example, the tip of a human subject's nose is in the median line.

Ipsilateral means on the same side, contralateral means on the other side and bilateral means on both sides. Structures that are close to the center of the body are proximal or central, while ones more distant are distal or peripheral. For example, the hands are at the distal end of the arms, while the shoulders are at the proximal ends.

A symmetric subject is assumed when the terms "medial," "lateral," "inferior," "superior," "anterior," and "posterior," are used to refer to an implant.

Embodiments disclosed herein relate to a method that can improve the positioning and fit of orthopedic reconstructive joint replacement implants. One of the goals in performing an orthopedic reconstructive joint replacement is to place a stem implant centrally within the bone and to provide good proximal fill. This not only more evenly loads the bone, but also eliminates the need for head position adjustment. Although specific explanations will refer to either the shoulder (humerus) or the hip (femur), the methods disclosed herein are mutually exclusive and can be used alone or in combination as a general method for reconstructing joints.

As will be described further herein, the embodiments of the stem implants and the methods for implantation and adjustment of the stem implants provide numerous advantages over the prior art. For example, referring to FIG. 1, a prior art stem implant 10 that is implanted into a humerus bone 12 is shown. During the implantation, a head 14 of the humerus bone 12 is resected in order to accommodate a tool (not shown) used to ream or broach a humeral canal 16 of the bone 12 in preparation for implantation. Once reamed, the humeral canal 16 defines a best fit diameter. The humeral canal 16 of the humerus bone 12 is then used as a guide to accept the stem implant 10. The stem implant 10 can include distal and proximal body portions 20, 22. In this regard, the distal body portion 22 of the stem implant 10 is inserted into the humeral canal 16 until the distal body portion 22 is tightly fitted into a distal area of the humeral canal 16.

Additionally, the proximal body portion 20 or head portion of the stem implant 10 is positioned in a proximal area 23 of the humeral canal 16.

Figure 2:
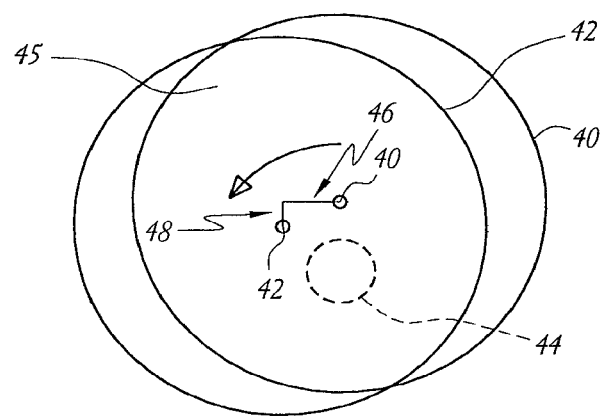
FIG. 2 is top view schematic illustration of a prior art eccentric head, which is used to adjust medial and posterior offset.

This prior art method poses several basic problems. First, because the distal body portion 22 is configured to form a tight fit with respect to the reamed humeral canal 16, the canal 16 dictates the position of the distal body portion 22 and therefore, the position of the proximal body portion 20 of the implant 10. Further, the proximal body portion 20 of such prior art implants does not fill the proximal area 23 of the humeral canal 16, and causes detrimental reliance on distal stem geometry and fit, as described below. With reference to FIG. 2, since the size, location, and orientation of the head portion 45 with respect to the humeral canal 16 vary greatly from person to person, a single stem geometry per size cannot accommodate natural placement or shape of the head portion 45. Consequently, as shown in the top axial view of the implant 10 of FIG. 2, adjustment of the positioning of the head portion 45 is often made by rotating the implant 10, for example, from a first position 40 to a second position 42 around an eccentric taper 44. Consequently, proximal fit of the head portion 45 on or in a resection plane 24 (shown in FIG. 1) of the humerus 12 is typically poor. Unfortunately, rotating an eccentric head 45 adjusts both posterior 46 and medial 48 head location at the same time, virtually excluding the possibility of perfect placement.

Figure 3:
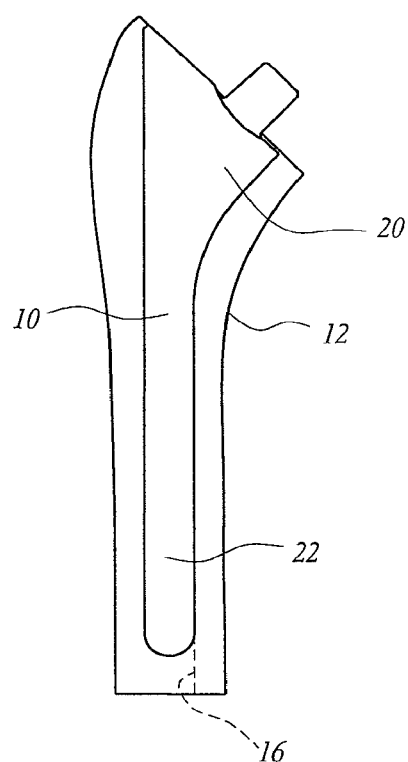
FIG. 3 is a cross-sectional side cross-sectional view of a prior art implant.
Figure 4:
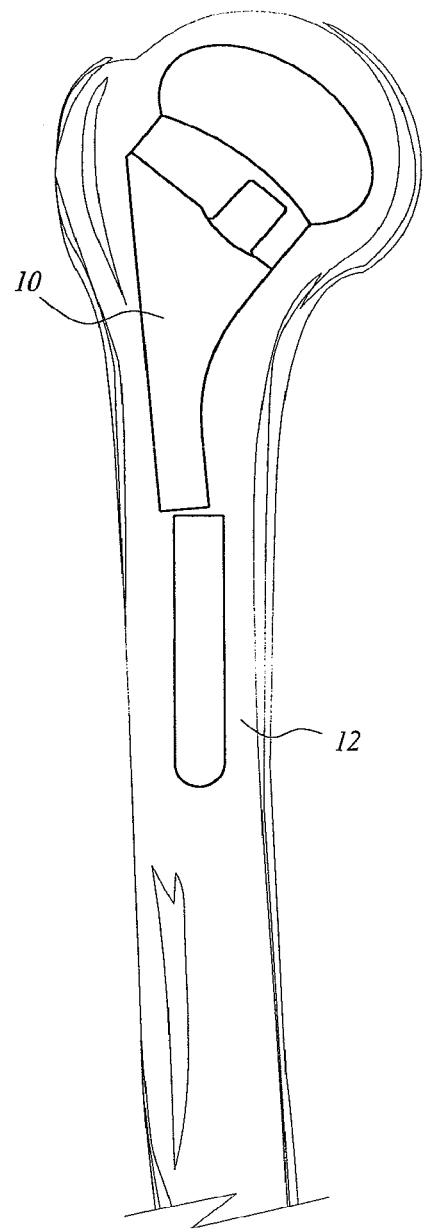
FIG. 4 is a side view of a humeral bone and implant illustrating stem fracture.

An additional problem in the prior art is that the position and orientation of the proximal body portion 20 are governed by the distal area of the canal 16, as shown in FIG. 3. As such, the proximal body portion 20 must be made small enough to fit the smallest possible envelope within the proximal area of the humerus 12. An excessively small proximal body portion 20 can cause poor proximal fixation of the implant 10 to the humerus 12 and lead to over-reliance on distal fixation of the implant 10. Over time, when too much emphasis is placed on distal fixation, the strength of the proximal area of the bone 12 begins to deteriorate. This, as shown in FIG. 4, can lead to loosening of the stem implant 10 and potentially fracture of the implant 10.

Figure 5A:
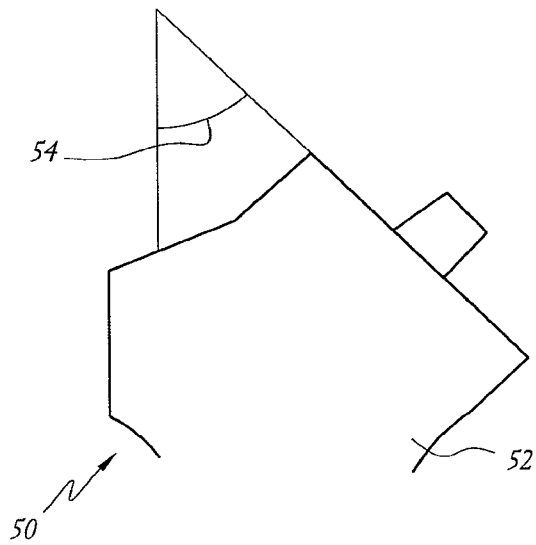
FIG. 5A is a side view of a prior art implant illustrating a unique head orientation of a proximal portion thereof.
Figure 5B:
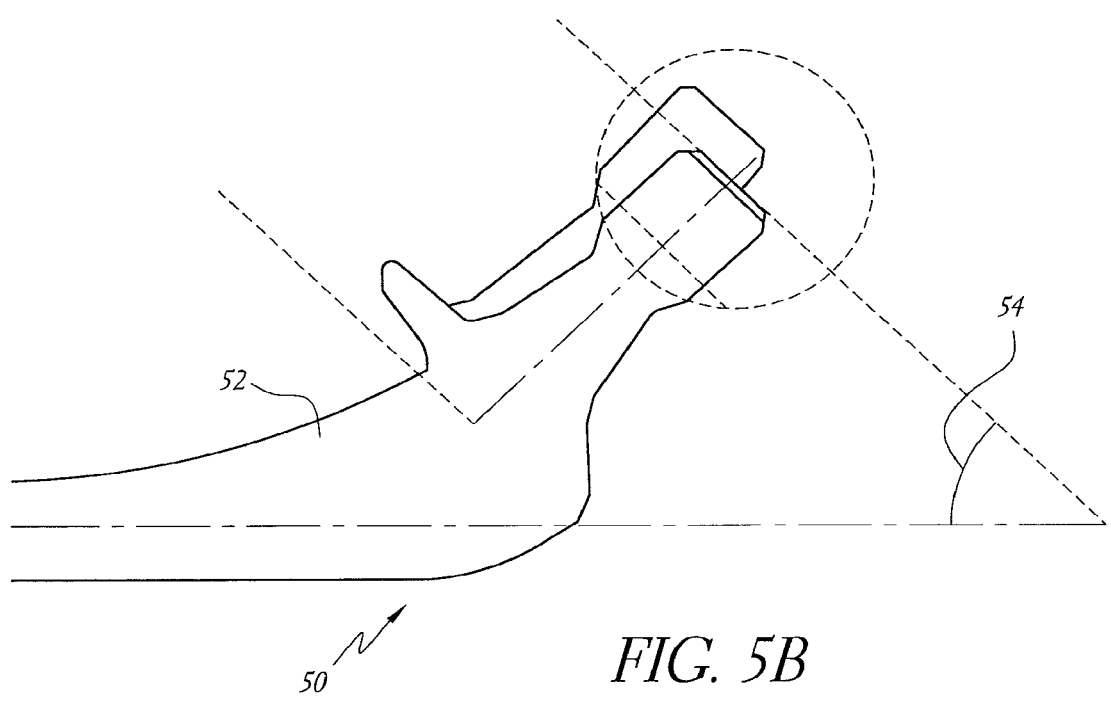
FIG. 5B is a side view of another prior art implant illustrating a unique head orientation of a proximal portion thereof.

While some companies have tried to improve upon this model by offering different neck angles, such as with implants 50 having different configurations, as illustratively shown in FIGS. 5A-B. As illustrated, such implants 50 use the same geometry for the proximal body portion 52 and simply vary a resection angle 54 of the implant 50. While this may improve placement of the head portion, it offers little to accommodate varying shapes of the proximal body portion 52.

In contrast, according several embodiments of the present inventions, it is contemplated that an angle of a distal section of a stem implant can be varied with respect to an entire proximal body instead of changing an angle of a resection cut or a neck. This means that, for different distal angles, the proximal body will move with respect to the humeral canal.

Figure 6A:
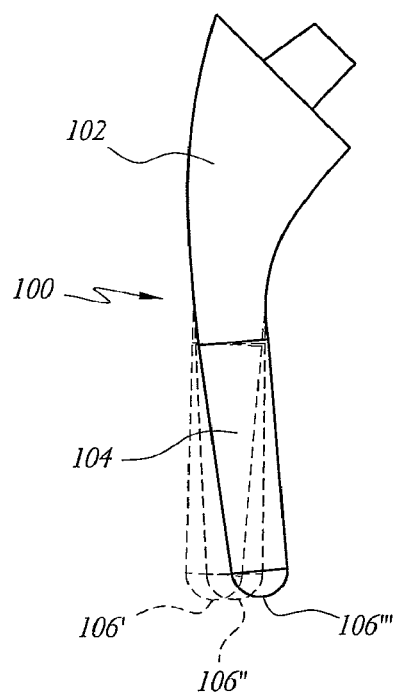
FIG. 6A is a side view of an embodiment of a humeral stem having certain features and advantages according to the present inventions.
Figure 6B:
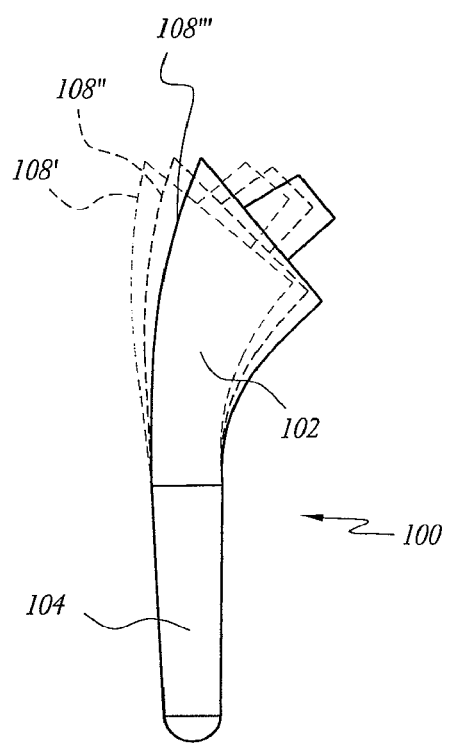
FIG. 6B is a side view of another embodiment of a humeral stem having certain features and advantages.

Referring now to FIGS. 6A-B, an embodiment of a stem implant 100 is shown. The stem implant 100 defines a proximal body 102 and a distal body 104. In FIG. 6A, it is illustrated that in some embodiments, the distal body 104 of the implant 100 can be configured at a variety of angular orientations 106', 106", 106'" relative to the proximal body 102. The result, as shown in FIG. 6B, is that the proximal body 102 of the implant 100 can be configured at a variety of angular orientations 108', 108", 108'" relative to the proximal body 102. Thus, it is contemplated that in some embodiments, a plurality of implants 100 can be provided to a surgeon such that the surgeon can select one of the implants 100 depending on the configuration required for the implant procedure. In another embodiment, the surgeon can be provided with a kit that comprises a variety of implants 100 with a variety of angular orientations 108', 108", 108'" relative to the proximal body 102.

Figure 7:
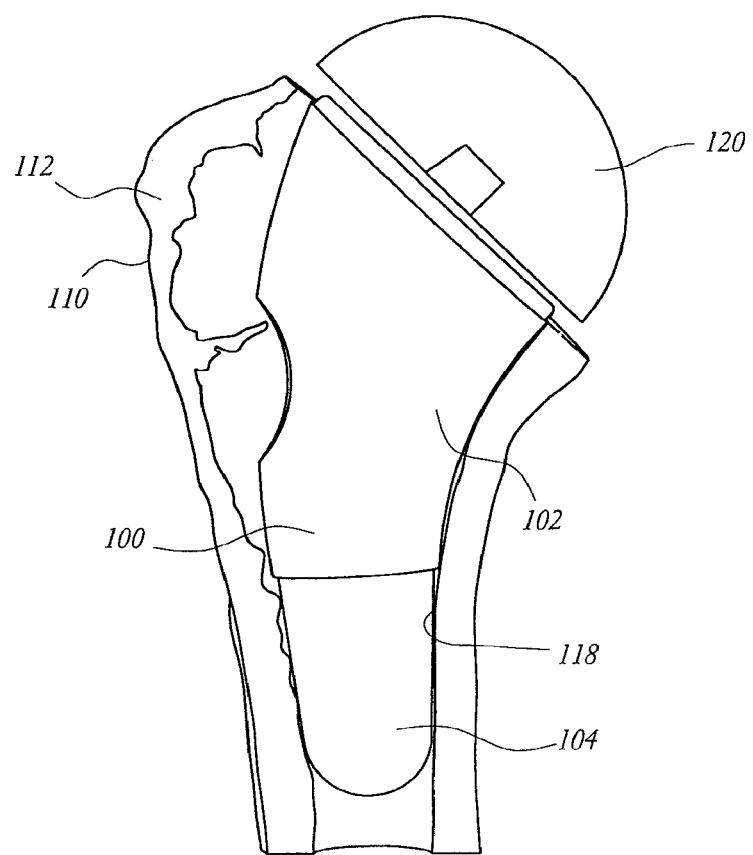
FIG. 7 is a side view of a humeral stem positioned within a proximal humerus, according to another embodiment.

In this regard, FIG. 7 illustrates that the stem 100 can be selected based on the shape and sizing of the proximal body 102 and the angle of the humeral canal, which is accommodated with one of the implants 100 that provides the best fitting distal angle from a selection of multiple angles. In this regard, because in some embodiments, the proximal body 102 need not be fitted at a single orientation into the humerus bone 110, the proximal body 102 can be larger and more conforming with a cortical portion 112 of the humerus bone 110, thus providing better proximal fixation and bone loading. Additionally, as illustrated in FIG. 7, the proximal body 102 is more conforming to the shape a cavity 118 of the humerus 110, and the stem 100 will tend to center itself during insertion, accommodating proper placement of the stem 100 and potentially eliminating the need for offset adjustment of a head 120 of the stem 100.

Furthermore, the stem sizes of embodiments disclosed herein can be based on a continuous and progressive curvature. For example, referring to FIG. 8, a single broach 130 could be used to prepare the cavity 118 of the humerus 110 for multiple sizes, simply by adjusting the depth that the broach 130 is inserted. The prior art implants referred to above currently require a different broach for each size, and in order to determine the proper size for use with a particular patient, one must experiment with multiple broaches, which can make it difficult to determine whether the next size is too large.

Figure 8:
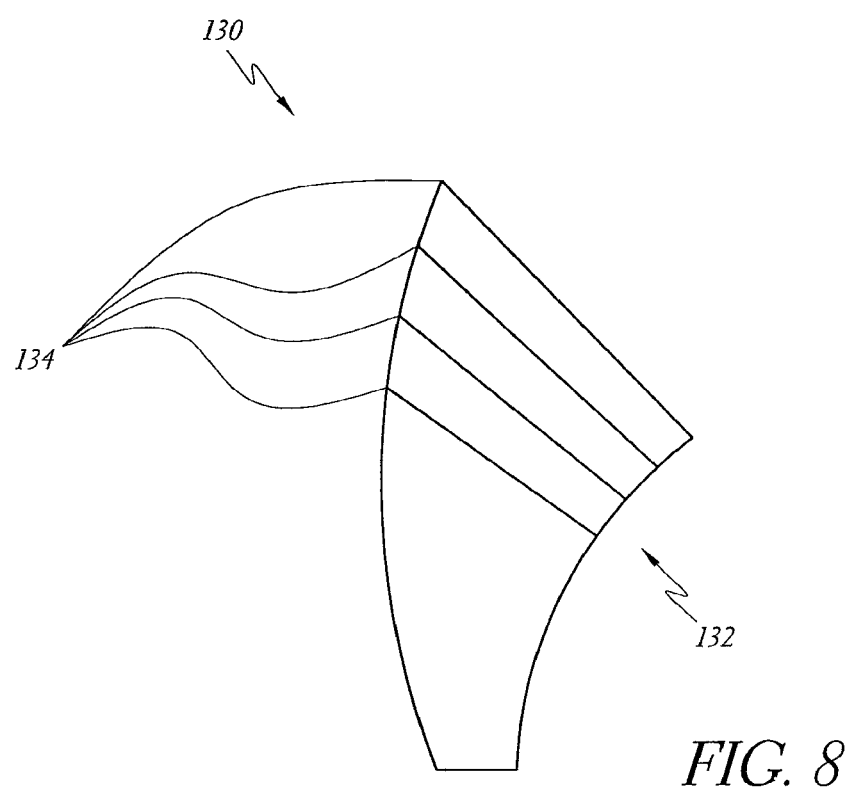
FIG. 8 is a schematic illustration of a proximal end of a broach, according to an embodiment.

However, as illustrated in FIG. 8, an embodiment disclosed herein provides for a broach 130 having a progressive curvature. The broach 130 can be used to prepare the cavity 118 of the bone 110 for implants 100 of any size. The broach 130 can be configured to include a depth indicator 132, which can comprise a plurality of markings 134. Thus, as the broach 130 is inserted into the humerus 110, the surgeon can broach the cavity 118 to a desired depth, and be aided in such broaching by the indication provided by the depth indicator 132.

Figure 9A:
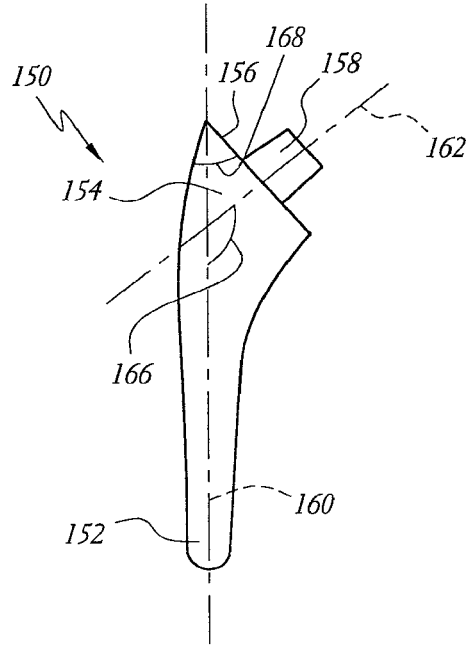
FIG. 9A illustrates a humeral stem, according to another embodiment.

The stem implant of embodiments disclosed herein can be variously configured depending on the intended use of the implant. For example, FIG. 9A illustrates an embodiment of a stem implant 150 for use in a shoulder prosthesis. As shown, the implant 150 can comprise: a distal section 152 (optional stems without the distal section 152 can be used); a proximal section 154; a resection plane or neck 156; and a coupling device 158.

As noted above, various configurations of the implant 150 can also be provided such that a surgeon can use a particularly configured implant 150 that suits the shape of the humeral cavity. Such variations in the implant 150 can be performed by altering the angular orientation of the distal section 152 and the proximal section 154 with respect to each other. For example, as shown in FIG. 9A, the distal section 152 of the implant 150 can define a longitudinal axis 160 and the proximal section 154 of the implant 150 can define a neck axis 162. In this regard, various configurations of the implant 150 can be designed with the longitudinal axis 160 of the distal section 152 being placed at a discrete angle 166 with respect to the neck axis 162 of the proximal section 154. Additional embodiments of the implant 150 can be configured with the longitudinal axis 162 of the distal section 152 being oriented at another discrete angle 168 with respect to the resection plane 156. However, it is contemplated that in yet other embodiments, the angle 166 can be varied while the angle 168 remains constant, and vice versa. In contrast, prior art stems vary the angle between the resection plane and the longitudinal axis by simply varying the resection angle. In contrast, in the illustrate embodiment, the angle between the resection plane and the longitudinal axis is varied by adjusting the angle between the distal section of the stem and the proximal section such that in certain embodiments the entire proximal section is pivoted about a point.

In addition, other embodiments can be configured such that the distal section 152 is tapered. Further, the coupling device 158 can be a tapered shape or other device for attachment of the humeral or femoral head. As used herein, the term "tapered shape" can refer to a shape that is gradually narrower or thinner toward one end. The shape of the proximal portion 154 of the implant 150 can curve medially to approximate the contours of the natural proximal humerus (as noted and illustrated above with respect to the embodiment shown in FIG. 7) and allow self-centered broaching.

Figure 9B:
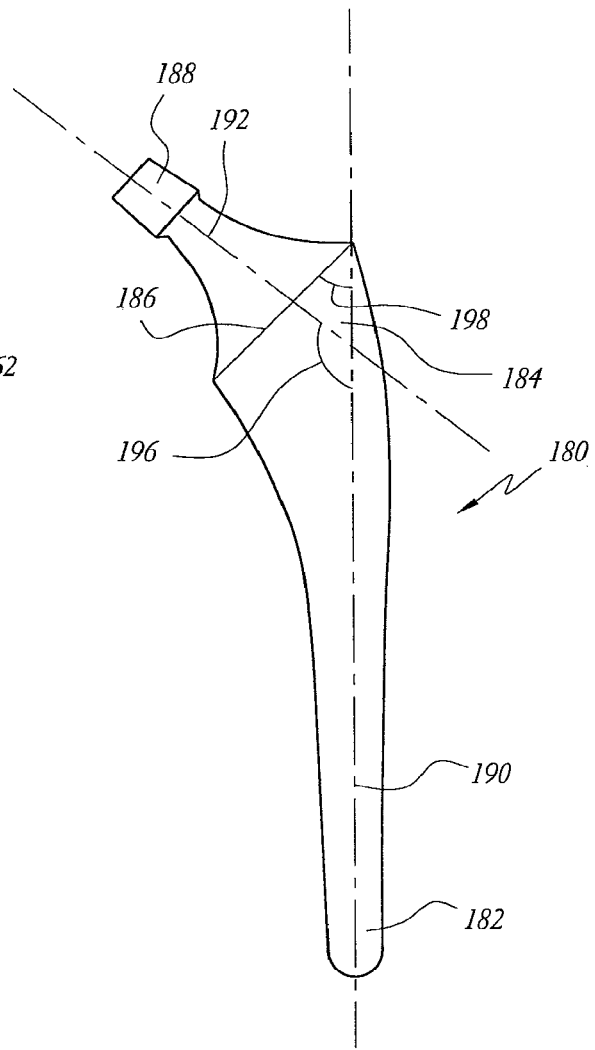
FIG. 9B illustrates a femoral stem, according to another embodiment.
Figure 10A:
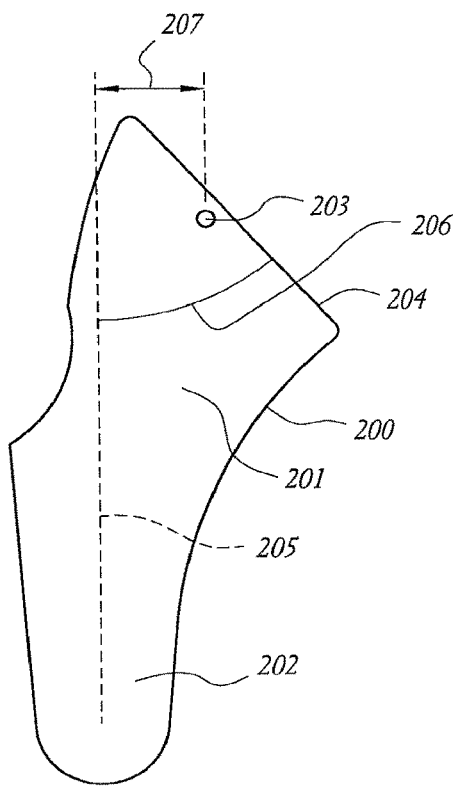
FIG. 10A is a side view of an embodiment of the stem wherein a proximal body portion thereof is oriented at an inclination angle with respect to a distal body portion thereof.
Figure 10B:
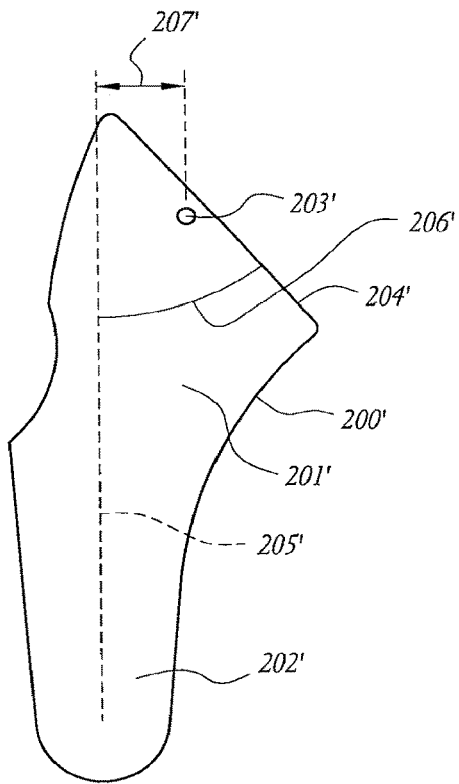
FIG. 10B is a side view of another embodiment of the stem wherein the proximal body portion is oriented at another inclination angle with respect to the distal body portion.
Figure 10C:
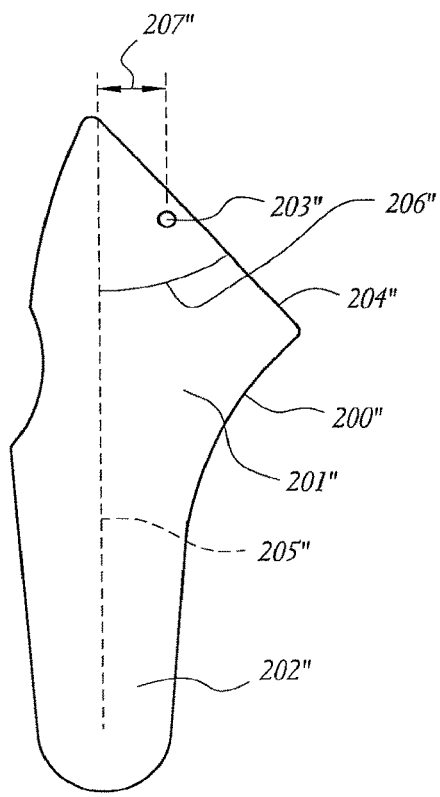
FIG. 10C is a side view of yet another embodiment of the stem wherein the proximal body portion is oriented at yet another inclination angle with respect to the distal body portion.
Figure 10D:
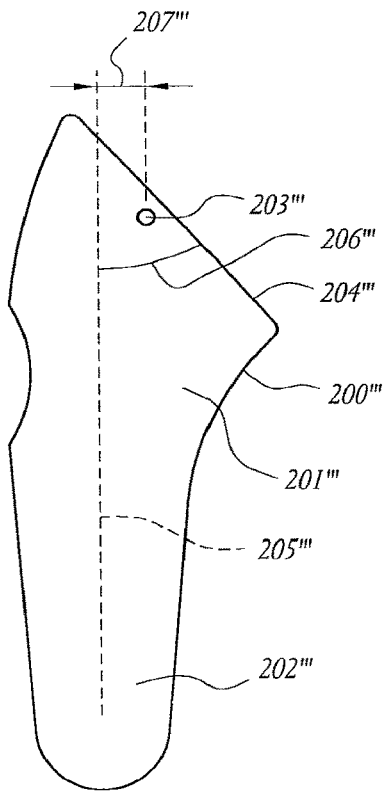
FIG. 10D is a side view of yet another embodiment of the stem wherein the proximal body portion is oriented at yet another inclination angle with respect to the distal body portion.

Referring now to FIG. 9B, an embodiment of a stem implant 180 for use in a hip prosthesis is shown. As shown, the hip stem implant 180 can comprise: a distal section 182 (optional stems without the distal section 182 can be used); a proximal section 184; a resection plane or neck 186; and a coupling device 188.

As noted above with respect to FIG. 9A, various configurations of the implant 180 can also be provided such that a surgeon can use a particularly configured implant 180 that suits the shape of the humeral cavity. Such variations in the implant 180 can be performed by altering the angular orientation of the distal section 182 and the proximal section 184 with respect to each other. For example, as shown in FIG. 9B, the distal section 182 of the implant 180 can define a longitudinal axis 190 and the proximal section 184 of the implant 180 can define a neck axis 192. In this regard, various configurations of the implant 180 can be designed with the longitudinal axis 190 of the distal section 182 being placed at a discrete angle 196 with respect to the neck axis 192 of the proximal section 184. Additional embodiments of the implant 180 can be configured with the longitudinal axis 190 of the distal section 182 being oriented at another discrete angle 198 with respect to the resection plane 186. However, it is contemplated that in yet other embodiments, the angle 196 can be varied while the angle 198 remains constant, and vice versa.

In addition, other embodiments can be configured such that the distal section 182 is tapered. Further, the coupling device 188 can be a tapered shape or other device for attachment of the humeral or femoral head. The shape of the proximal portion 184 of the implant 180 can curve medially to approximate the contours of the natural proximal humerus (as noted and illustrated above with respect to the embodiment shown in FIG. 7) and allow self-centered broaching.

FIGS. 10A-D illustrate an embodiment of a stem implant 200 comprising proximal and distal body portions 201, 202. As described above, and as illustrated in FIGS. 10A-D, it is contemplated that the proximal body portion 201 can be angularly oriented with respect to the distal body portion 202 at a plurality of angles, thus yielding a plurality of potential configurations of the stem implant, indicated as 200, 200', 200", and 200'". In accordance with the embodiment illustrated in FIGS. 10A-D, the proximal body portion 201 can define a head center 203 and a resection plane 204.

In some embodiments, the head center 203 can lie in the resection plane 204, and in particular, in a central location of the proximal body portion 201 in the resection plane 204. Further, the distal body portion 202 can define a longitudinal axis 205 that is oriented at an inclination angle 206 with respect to the resection plane 204. Furthermore, the head center 203 and the longitudinal axis 205 are spaced apart at a medial offset 207.

The medial offset 207, as shown, can be the distance between the head center 203 of the proximal body portion 201 and a closest point along the longitudinal axis 205. If illustrated graphically, the medial offset 207 would be the length of a line oriented perpendicularly to the longitudinal axis 205 and extending between the head center 203 and the longitudinal axis 205. Therefore, in accordance with a preferred embodiment, the stem implant 200 can be configured such that the inclination angle 206 remains constant while the medial offset 207 varies.

The medial offset 207 can be between approximately 4 mm and approximately 15 mm, and is preferably between approximately 5 mm to approximately 11 mm. In a system of stem implants 200, it is contemplated that a plurality of implants 200, such as four, can be provided, and that the implants can have medial offsets of approximately 5 mm, approximately 7 mm, approximately 9 mm, and approximately 11 mm, respectively. Accordingly, each implant would have a different medial offset, but all of the implants could have the same inclination angle. Other embodiments and combinations can be created by one of skill utilizing these teachings.

In accordance with another embodiment shown in FIGS. 11A-C, it is contemplated that the medial offset can vary as a function of the inclination angle. FIGS. 11A-C illustrate a system of implants 200', 200", and 200'". As similarly described with respect to the embodiment shown in FIG. 10, each of the implants 200', 200", and 200'" can include proximal and distal body portions 201', 201", 201'" and 202', 202", 202'", respectively, as well as medial offsets 207', 207", 207'" defined as the distance between head centers 203', 203", 203'" of the respective ones of the proximal body portions 201', 201", 201'" and longitudinal axes 205', 205", 205'" of the respective ones of the distal body portions 202', 202", 202'".

FIGS. 11A-C illustrate an embodiment of a system of implants 200', 200", 200'" wherein the medial offsets 207', 207", 207'" change as a function of inclination angle 206', 206", 206'", respectively. In the embodiment of FIG. 11A, the medial offset 207' is approximately 12 mm while the inclination angle 206' is approximately 45 degrees. In the embodiment of FIG. 11B, the medial offset 207" is approximately 8 mm while the inclination angle 206" is approximately 41 degrees. Finally, in the embodiment of FIG. 11C, the medial offset 207'" is approximately 5 mm while the inclination angle 206'" is approximately 37 degrees. These measurements are those of exemplary embodiments for purposes of illustration only. It is contemplated that the medial offset can be in the range of approximately 4 mm to approximately 15 mm, and that the inclination angle can be in the range of approximately 30 degrees to approximately 55 degrees.

Figure 12:
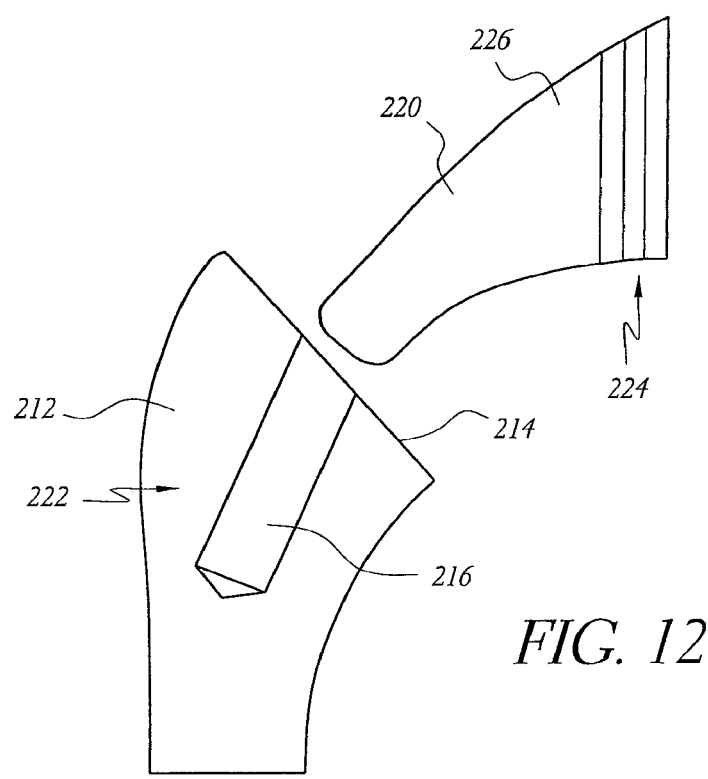
FIG. 12 shows how the broach can be inserted into the humerus.
Figure 13:
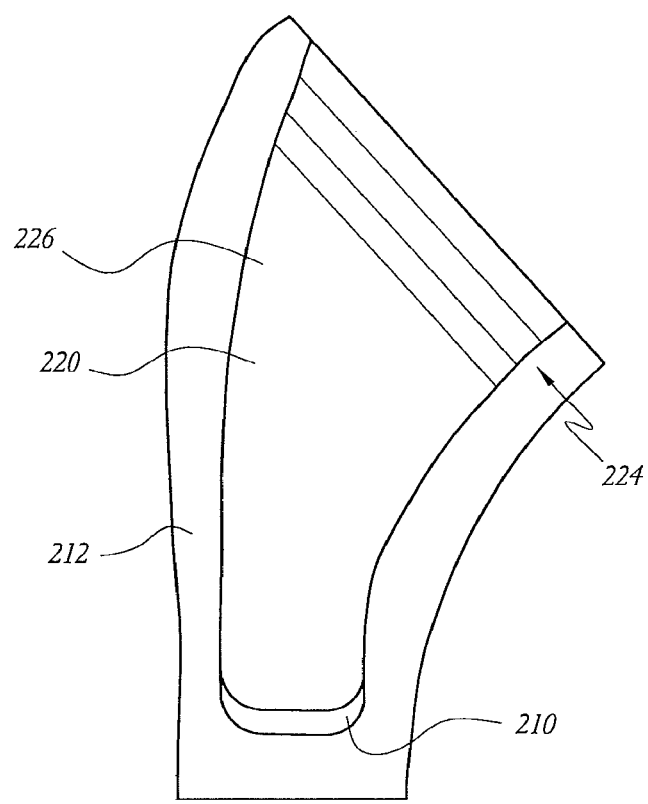
FIG. 13 shows the broach when it is fully inserted to the correct size marking.

Referring now to the cross-sectional views of FIGS. 12-13, an embodiment of a procedure will be described for preparing a humeral cavity 210 of a humerus bone 212 and implanting the stem into the prepared cavity 210. After the humeral head of the bone 212 is resected to define a resection surface 214, an initial or pilot hole 216 may be drilled in the center of the resected head. A broach 220 can then be inserted through a central area of the resection surface 214, through the pilot hole 216, and driven into the humerus 212 with a mallet or other impaction device. As the broach 220 is being driven in, it is guided by a proximal area 222 of the humerus bone 212. As discussed above, the broach 220 can be configured for use with multiple sizes, and a depth indicator 224, such as graduations, marking, or other visual or physical devices used on or with the broach 220. Thus, the surgeon can determine the necessary size of the implant required for the bone, and can then use a single broach 220 to broach the cavity 210 to the desired depth as needed. The depth indicator 224 can illustrate the depth or distance required to further insert the broach 220 in order to reach a given stem implant size, as illustrated in FIG. 13.

The sizing of a proximal body 226 of the broach 220 can be configured such that it increases in size in the proximal direction. Such increases in size can be progressive, if desired, depending on the geometry of the implants being used. Thus, one broach 220 could be used to prepare the cavity 210 for an implant of small size or of large size, depending on how much of the proximal body 226 of the broach 220 is inserted to within the bone 212 during preparation. Because of this, a single broach 220 can be used to prepare a cavity 210 for several sizes simply by changing the depth of insertion. This will make it very simple for a surgeon to determine the proper size. For example, if the broach is inserted for a size 3, the depth indicator 224 can show the location for a size such that the difference in insertion depth is clearly illustrated.

Figure 14:
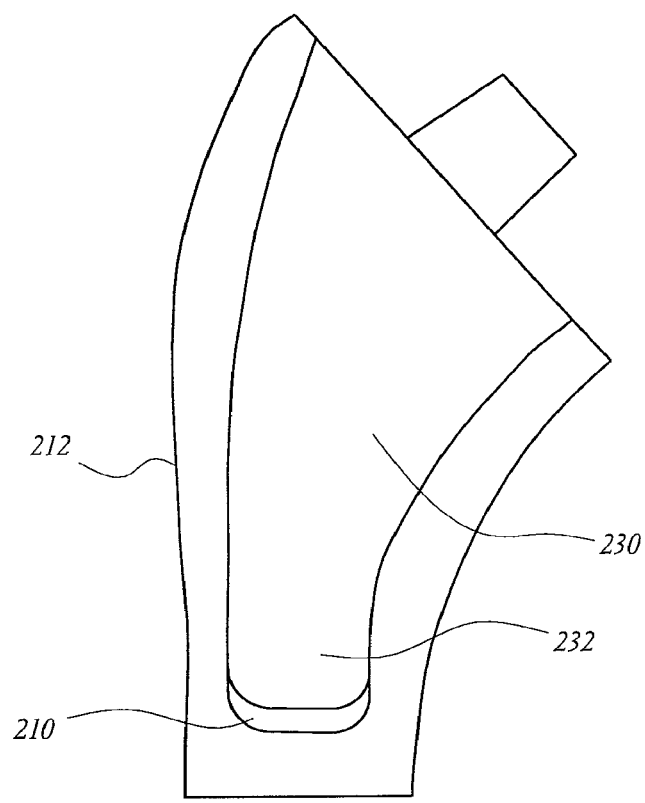
FIG. 14 shows a stem with a shortened distal region.

It is also contemplated that during the preparation of the cavity 210, the surgeon may trial one or many implants to determine what size of the distal portion of the implant is necessary. If the surgeon feels that stem stability will be sufficient without the distal portion, he/she may opt to stop the preparation of the cavity 210 at that point and implant a short stem. Thus, the surgeon can exercise caution and discretion in incrementally reaming the cavity 210 so that a stem 230 with a shorter distal portion 232 can be used if desired, as shown in FIG. 14.

Figure 15:
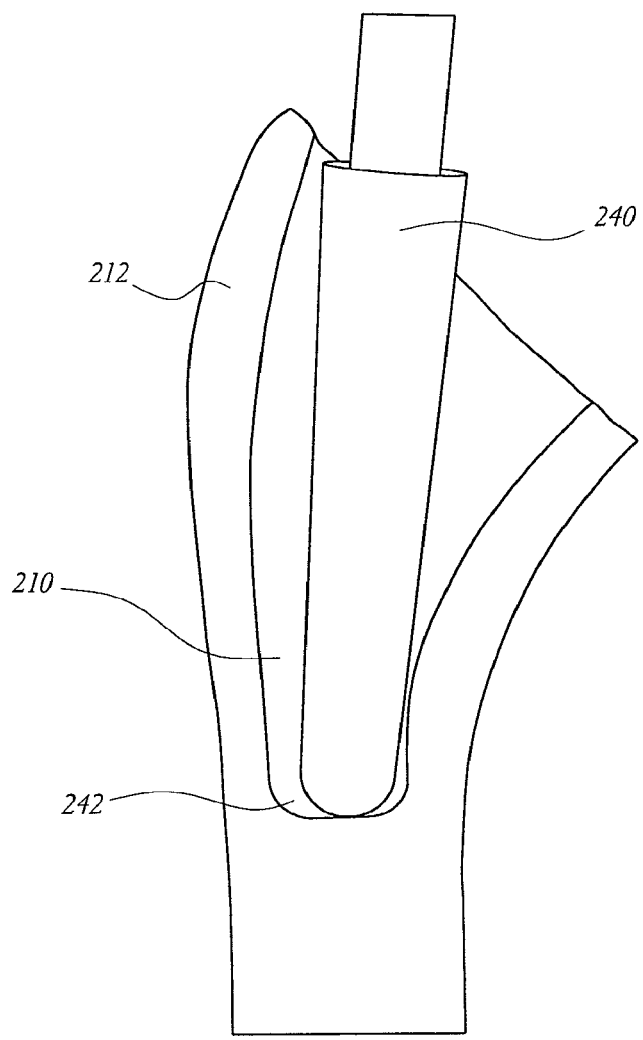
FIG. 15 shows how a reamer is inserted into a broached humeral cavity.

Referring now to FIG. 15, if the surgeon opts to use a stem with a distal section, the next step is to ream the canal 210 of the humerus 212 using a tapered or cylindrical reamer 240. The reamer 240 is inserted into the humeral canal 210 at a base 242 of the cavity 210 and reamed to a desired depth. Once the canal 210 has been reamed to its proper depth, a trial of the reamer 240 can be used to determine which of the angled stems is needed, and the stem can then be implanted.

As noted above, once the proximal section of the humeral canal has been prepared, the humeral canal must be reamed if a stem with a distal section is to be used. As also mentioned above, the angle of the stem of the certain embodiments can be adjusted by varying the angle of the distal section with respect to the proximal body. Because of this, instead of fitting the stem to the humeral canal and forcing a non-conforming proximal body to be poorly placed in the humerus, a conforming proximal body can be fit to the proximal humerus and different distal stem angles can be used to fit the canal. In some embodiments, a set of stems can be provided that have three discrete stem angles of approximately 35, approximately 40, and approximately 45 degrees (as measured between the longitudinal axis and the resection plane, discussed in FIGS. 9A-B). Alternate embodiments comprising more angles and/or a wider range also may be used. With a five degree interval between angles, a maximum 2.5 degree mismatch could exist between the stem distal angle and the humeral canal; however, such a mismatch could still allow proper placement of the stem. In some embodiments, the distal portions of the reamer and the stem implant can be tapered to help accommodate this difference.

Wolff's law states that when bone is repeatedly stressed, it becomes stronger, harder, and denser. Because the outside of a given bone typically carries the majority of the load, the bone tends to get much stronger towards the outside. Conventional shoulder stems do not attempt to approximate the shape of the proximal body of the humerus. Instead, they force the broach to be inserted into the bone at a certain position and in a certain direction, not taking advantage of the above-mentioned strength properties of the bone.

Figure 16:
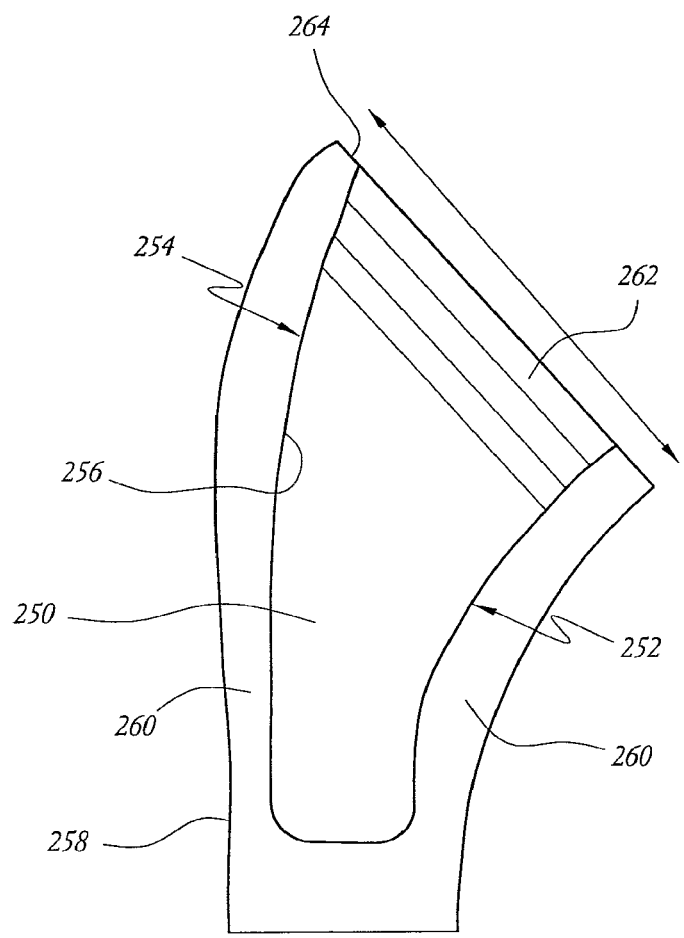
FIG. 16 shows how the broach is guided by the conforming proximal humerus.

In contrast, as illustrated in the embodiment of FIG. 16, a broach 250 can be configured to have a medial curve/surface 252 and a lateral curve/surface 254 that are configured to provide the broach 250 with a shape that facilitates proper alignment of the stem 250 within a cavity 256 of a bone 258 such that the broach 250 can be centered within a cortical portion 260 of the bone 258. Thus, the medial curve 252, and to a somewhat lesser extent, the lateral curve 254, can be designed to mimic the general shape of the proximal area of the humerus 258.

Due to the shaping of such embodiments of the broach 250, the broach 250 will want to follow the path of least resistance, which will be through the weakest bone at the center of the humerus 258 and not through the cortical portion 260 thereof. The final result is that a proximal body 262 of the broach 250 can be placed in the center of a resected surface 264 of the humerus 258 regardless of its position with respect to the humeral canal 256. Further, it is also contemplated that proximal bodies 262 of large sizes can be used and that they will be supported by more structural bone than a traditional humeral stem. Since the proximal body 262 can be placed essentially in the center of the humerus 258, little or no adjustment of the proximal portion 262 will be required.

While the present inventions have been described with reference to the specific embodiments, it should be understood by those skilled in the art that various changes may be made and equivalents may be substituted without departing from the true spirit and scope of the inventions. In addition, many modifications may be made to adopt a particular situation, material, composition of matter, process, process step or steps, to the objective spirit and scope of the present inventions. All such modifications are intended to be within the scope of the claims appended hereto.

For example, in another embodiment, a reamer guide could be placed into the prepared proximal cavity to eliminate any angular mismatch between sizes instead of reaming using the canal for guidance. Similarly, in other embodiments of the present inventions, more angled stems could be added to reduce the potential for mismatch.

In other embodiments, the humeral canal could be reamed and the proximal cavity could be broached using the reamer for guidance, instead of broaching before reaming. While this could somewhat influence proximal stem placement, the benefit of multiple distal angles would still vastly improve placement and fill over current stems.

In yet other embodiments, curves that mimic the proximal body shape could be used in areas other than the medial and lateral curves/surfaces. They could be placed anterior and posterior or at any number of regular intervals around the stem.

In yet another embodiment, the distal stem shape could also have a local increase in size at its tip (such as, but not limited to, a ball on the end of the distal section). This would help accommodate any mismatch between the distal section and the reamed humeral canal. The distal increase would contact the reamed cavity and the gap after the increase would allow the distal stem center to vary slightly from the humeral canal center.

In other embodiments, the shape of the distal section of the stem and/or reamer can be cylindrical, elliptical, or irregularly shaped instead of being tapered. As used herein, the term "elliptical" can refer to a shape that resembles an elongated or flattened circle; the term "cylindrical" can refer to a shape that is round in cross section, and equally wide throughout its length; and the term "irregularly shaped" can refer to a shape that does not vary consistently in shape or size, for example, a distal region that is substantially tapered, but has one area that has a significantly increased size.

In other embodiments, the shape of the distal section of the stem and/or reamer can incorporate any grooves, slots, or cutouts for flexibility, fit, or fixation. As used herein, the term "groove" can refer to an elongated channel in the distal region of the stem. These grooves are typically narrow and distributed around the distal region at close intervals, creating narrow raised ridges between them. When inserted with slight interference with the bone, these ridges can embed themselves within the bone, providing mechanical locking and allowing a tight fit with some mismatch in shape between the canal and the distal region. As used herein, the term "slot" can refer to an elongated opening in the distal region of the stem placed to increase the flexibility of that portion of the stem. If a single slot is used, it can extend through the entire thickness of the distal region of the stem, dividing it in two. If multiple slots are used, they can intersect and end near the central axis of the distal region of the stem, dividing the distal region in as many sections as there are slots. As used herein, the term "cut out" can refer to a recess in the distal region of the stem that is meant to increase the flexibility of that portion of the stem. These cutouts are typically on one or more sides of distal region of the stem and are placed around the periphery, not through the center.

In other embodiments, the entire cavity could be prepared by broaching instead of by broaching and then reaming.

In other embodiments, the cavity could be broached first and then reamed using a reamer that was guided by the broach or ream first and use a broach that was guided by the reamer instead of broaching and reaming independently.

Figure 17:
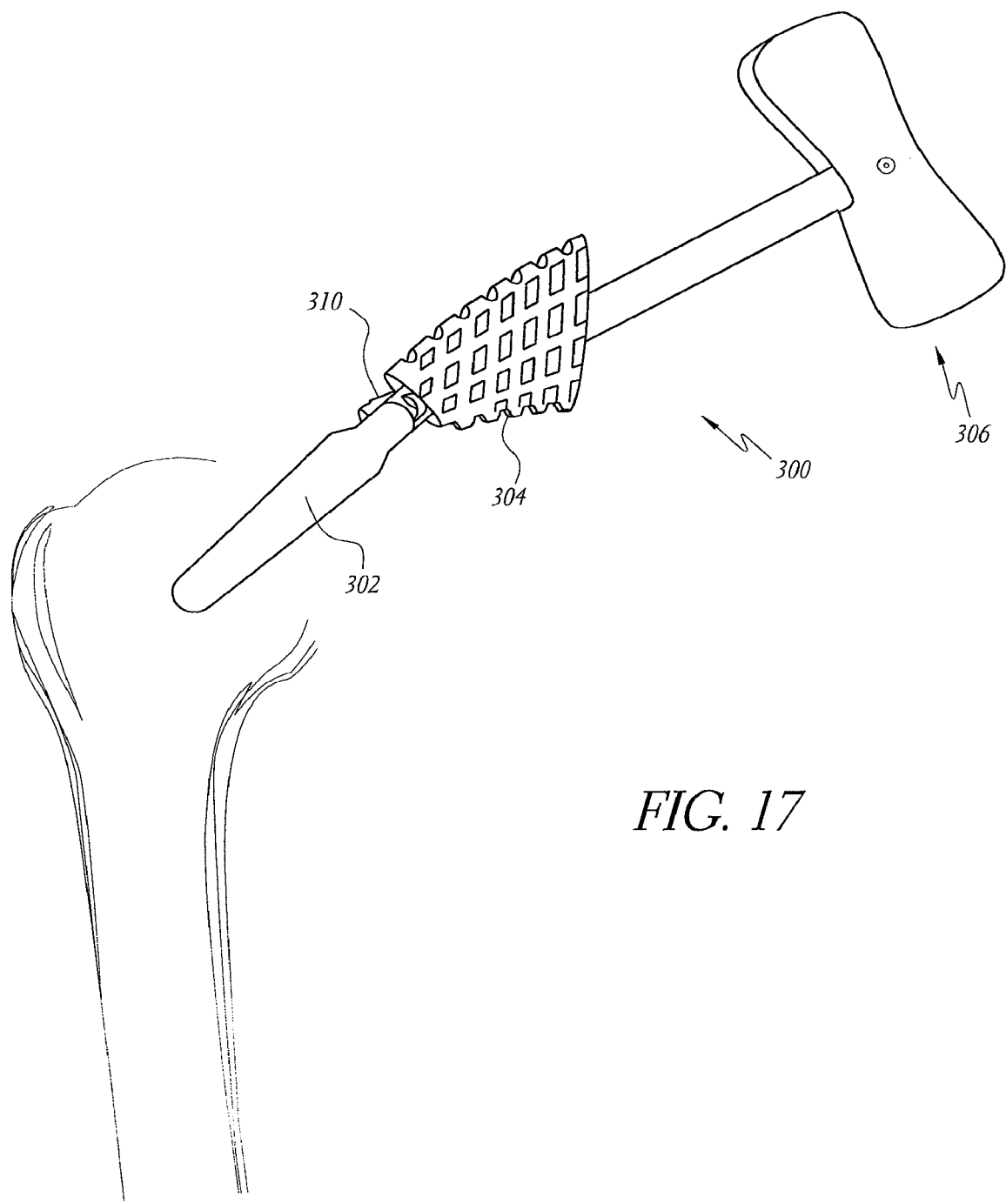
FIG. 17 shows an instrument that combines a broach and a reamer.

In yet another embodiment illustrated in FIG. 17, an instrument 300 is provide that incorporates a reaming section 302 and a broaching section 304 that are coupled together with a handle or driving member 306. The reaming section 302 can be disposed at a distal end of the instrument 300 and be used to ream the bone for preparation thereof for implantation. The broaching section 304 can incorporate a broach and be disposed intermediate the reaming section 302 and the handle 306, such that during use, after the reaming section 302 has reamed the cavity of the bone, the instrument 300 can continue to be driven into the bone such that the broaching section 304 can be used to broach a proximal portion of the cavity. In this regard, a single tool can be used to perform both of the broaching and reaming operations in preparation for implantation of a stem. Further, the instrument 300 can incorporate a joint 310 that would allow for slight angular adjustments of the orientation of the reaming section 302 relative to the broaching section 304.

In other embodiments, the distal region of the stem could be angled in the anterior/posterior direction as well as the medial/lateral direction, In other embodiments, the neck of the stem, particularly a hip stem, could be made modular, such that a given stem would accept multiple necks that would be fixed to the stem using a taper or other locking mechanism.

Where a range of values is provided, it is understood that each intervening value, to the tenth of the unit of the lower limit unless the context clearly dictates otherwise, between the upper and lower limit of that range and any other stated or intervening value in that stated range is encompassed within the inventions. The upper and lower limits of these smaller ranges which may independently be included in the smaller ranges is also encompassed within the inventions, subject to any specifically excluded limit in the stated range. Where the stated range includes one or both of the limits, ranges excluding either both of those included limits are also included in the inventions.

Unless defined otherwise, all technical and scientific terms used herein have the same meaning as commonly understood by one of ordinary skill in the art to which this inventions belongs. Although any methods and materials similar or equivalent to those described herein can also be used in the practice or testing of the present inventions, the preferred methods and materials are now described. All publications mentioned herein are incorporated herein by reference to disclose and described the methods and/or materials in connection with which the publications are cited.

It must be noted that as used herein and in the appended claims, the singular forms "a" "and," and "the" include plural references unless the context clearly dictates otherwise. All technical and scientific terms used herein have the same meaning.

The publications discussed herein are provided solely for their disclosure prior to the filing date of the present application. Nothing herein is to be construed as an admission that the present inventions is not entitled to antedate such publication by virtue of prior invention. Further, the dates of publication provided may be different from the actual publication dates which may need to be independently confirmed.

Although these inventions have been disclosed in the context of certain preferred embodiments and examples, it will be understood by those skilled in the art that the present inventions extend beyond the specifically disclosed embodiments to other alternative embodiments and/or uses of the inventions and obvious modifications and equivalents thereof. In addition, while several variations of the inventions have been shown and described in detail, other modifications, which are within the scope of these inventions, will be readily apparent to those of skill in the art based upon this disclosure. It is also contemplated that various combination or sub-combinations of the specific features and aspects of the embodiments may be made and still fall within the scope of the inventions. It should be understood that various features and aspects of the disclosed embodiments can be combined with or substituted for one another in order to form varying modes of the disclosed inventions. Thus, it is intended that the scope of at least some of the present inventions herein disclosed should not be limited by the particular disclosed embodiments described above.

What is claimed is:

1. A system of orthopedic devices for joint reconstruction surgery, the system comprising:
    an articular component;
    a plurality of stem components, each stem component comprising:

a distal body portion configured to be inserted into a central cavity region created in a bone of the joint, the distal body portion defining a longitudinal axis; and a proximal body portion defining a resection plane configured to be disposed in-plane with a resection surface of a bone when applied to a patient, the longitudinal axis extending through the resection plane, the resection plane defining a proximal-most limit of the proximal body, the proximal-most limit disposed in-plane with the resection surface of the bone, the proximal body for supporting a head the articular component that in turn has a geometric center positioned within the proximal body portion or at the resection plane, the proximal body portion having a contour extending from the resection plane toward the distal body portion, the geometric center being spaced from the longitudinal axis at a medial offset distance based on the contour of the proximal body portion, and the resection plane oriented at an inclination angle with respect to the longitudinal axis; and wherein at least two of the plurality of stem components include different medial offset distances; and wherein each stem component of the system having different medial offset distances is configured such that as the medial offset increases the inclination angle remains constant.

2. The system of claim 1, the particular component comprising a convex articular surface.

3. The system of claim 1, wherein the system includes at least four stem components.

4. The system of claim 1, wherein the plurality of stem components comprises:
a first stem component has a medial offset of approximately 5 mm,
a second stem component has a medial offset of approximately 7 mm,
a third stem component has a medial offset of approximately 9 mm, and
a fourth stem component has a medial offset of approximately 11 mm.

5. The system of claim 1, wherein each of the stem components of the system has a medial offset of between approximately 4 mm and approximately 15 mm.

6. The system of claim 1, wherein the inclination angle of each stem component is between approximately 30 degrees and approximately 55 degrees.

7. The system of claim 1, wherein the distal body portion and the proximal body portion form a single piece.

8. The system of claim 1, wherein the geometric center lies in the resection plane.

9. The system of claim 1, wherein each stem component is configured to be inserted into a central cavity region of a humerus.

10. The system of claim 1, wherein each stem component is configured to be inserted into a central cavity region of a femur.

11. The system of claim 1, wherein the proximal body portion is configured to support the head component without requiring an exposed taper connection at a location medial of the resection surface of the bone.

12. A system of orthopedic devices for joint reconstruction surgery, the system comprising: an articular component a plurality of stems, each stem comprising: a distinct distal body portion configured to be inserted into a central cavity region created in a bone of the joint, the distal body portion defining a longitudinal axis;

and a proximal body portion defining a planar surface for supporting the articular component that in turn has a geometric center positioned within the proximal body portion, the planar surface extending from a medial boundary of said stem and a lateral boundary of said stem, and configured to be aligned with a resection surface of a humerus when the stem is implanted, and the proximal body portion having a contour extending from the planar surface toward the corresponding distal body portion, the geometric center being spaced from the longitudinal axis at a medial offset distance based on the contour of the proximal body portion, and the planar surface of the stem oriented at an inclination angle with respect to the longitudinal axis; wherein at least one of the plurality of stems of the system is configured with a larger medial offset than another one of the plurality of stems, and wherein the inclination angle of the at least one of the plurality of stems and the other one of the plurality of stems remains constant.

13. The system of claim 12, the articular component comprising a convex articular surface.

14. The system of claim 12, wherein the system includes at least four stems.

15. The system of claim 12, wherein the plurality of stems comprise:
a first stem has a medial offset of approximately 5 mm,
a second stem has a medial offset of approximately 7 mm,
a third stem has a medial offset of approximately 9 mm, and
a fourth stem has a medial offset of approximately 11 mm.

16. The system of claim 12, wherein each of the stems of the system has a medial offset of between approximately 4 mm and approximately 15 mm.

17. A system of orthopedic devices for joint reconstructive surgery, the system comprising:
an articular component;
a first stem comprising:
a first distal body portion configured to be inserted into a central cavity region created in a bone of the joint, the first distal body portion defining a first longitudinal axis,
a first proximal body portion for supporting the articular component, the articular component having a geometric center positioned within the first proximal body portion when supported by the first proximal body portion, the first proximal body portion having a medial contour extending toward the first distal body portion, the geometric center being spaced from the first longitudinal axis at a first medial offset distance based on the medial contour of the first proximal body portion, the first stem configured to support the articular component at a first inclination angle with respect to the first longitudinal axis, and
wherein the first proximal body portion defines a first resection plane configured to be disposed in-plane with a resection surface of the bone, the first longitudinal axis extending through the first resection plane;
a second stem comprising:
a second distal body portion configured to be inserted into the central cavity region created in the bone of the joint, the second distal body portion defining a second longitudinal axis, a second proximal body portion for supporting the articular component, the geometric center of the articular component positioned within the second proximal body portion when supported by the second proximal body portion, the second proximal body portion having a medial contour extending toward the second distal body portion, the geometric center being spaced from the second longitudinal axis at a second medial offset distance based on the medial contour of the second proximal body portion, the second stem configured to support the articular component at a second inclination angle with respect to the second longitudinal axis, and wherein the second proximal body portion defines a second resection plane configured to be disposed in-plane with the resection surface of the bone, the second longitudinal axis extending through the section resection plane;

wherein the first medial offset is greater than the second medial offset; and wherein the first inclination angle is the same as the second inclination angle.

18. The system of claim 17, the articular component comprising a convex articular surface.

19. The system of claim 17, wherein the system includes at least four stem stems.

20. The system of claim 17, wherein the first medial offset and the second medial offset are between approximately 4 mm and approximately 15 mm.

\* \* \* \* \*